(12) United States Patent
Kim et al.

(10) Patent No.: US 8,076,377 B2
(45) Date of Patent: Dec. 13, 2011

(54) N,N-DIMETHYL IMIDODICARBONIMIDIC DIAMIDE DICARBOXYLATE, METHOD FOR PRODUCING THE SAME AND PHARMACEUTICAL COMPOSITIONS COMPRISING THE SAME

(75) Inventors: Sung Wuk Kim, Gyeonggi-do (KR); Sung Soo Jun, Gyeonggi-do (KR); Young Gwan Jo, Daejeon (KR); Ja Seong Koo, Daejeon (KR); Young Woong Kim, Daejeon (KR); Byoung Ha Kim, Daejeon (KR); Duck Kim, Daegu (KR)

(73) Assignee: Hanall Pharmaceutical Company, Ltd., Daejeon (KR)

( * ) Notice: Subject to any disclaimer, the term of this patent is extended or adjusted under 35 U.S.C. 154(b) by 0 days.

(21) Appl. No.: 12/733,711

(22) PCT Filed: Sep. 19, 2008

(86) PCT No.: PCT/KR2008/005574
§ 371 (c)(1),
(2), (4) Date: Mar. 16, 2010

(87) PCT Pub. No.: WO2009/038396
PCT Pub. Date: Mar. 26, 2009

(65) Prior Publication Data
US 2010/0249241 A1    Sep. 30, 2010

(30) Foreign Application Priority Data

Sep. 21, 2007 (KR) .......... 10-2007-0096527
Sep. 21, 2007 (KR) .......... 10-2007-0096533
Jun. 30, 2008 (KR) .......... 10-2008-0062806

(51) Int. Cl.
*A01N 37/52* (2006.01)
*A01N 37/10* (2006.01)
*A61K 31/155* (2006.01)
*A61K 31/235* (2006.01)

(52) U.S. Cl. ................ 514/635; 514/554

(58) Field of Classification Search ............ None
See application file for complete search history.

(56) References Cited

U.S. PATENT DOCUMENTS

| | | | |
|---|---|---|---|
| 3,903,141 A | 9/1975 | Just et al. | |
| 3,957,853 A | 5/1976 | Bohuon | |
| 4,028,402 A | 6/1977 | Fischer et al. | |
| 4,080,472 A | 3/1978 | Bohuon | |
| 4,835,184 A | 5/1989 | Hugelin et al. | |
| 4,879,303 A | 11/1989 | Davison et al. | |
| 6,031,004 A | 2/2000 | Timmins et al. | |
| 6,399,658 B1 * | 6/2002 | Noguchi et al. | 514/474 |
| 2003/0220301 A1 | 11/2003 | Lal et al. | |

FOREIGN PATENT DOCUMENTS

| | | |
|---|---|---|
| CN | 1962661 A | 5/2007 |
| WO | WO-99/29314 A1 | 6/1999 |
| WO | WO-99/47128 A1 | 9/1999 |
| WO | WO-02/12177 A1 | 2/2002 |
| WO | WO-2005/033067 A1 | 4/2005 |

OTHER PUBLICATIONS

"International Application Serial No. PCT/KR2008/005574, International Search Report mailed Mar. 17, 2009", 2 pgs.

Buzzai, M., et al., "Systematic Treatment with the Antidiabetic Drug Metformin Selectively Impairs p53-Deficient Tumor Cell Growth", *Cancer Research*, 67(14), (2007), 6745-6752.

* cited by examiner

*Primary Examiner* — Daniel Sullivan
*Assistant Examiner* — Jennifer C Sawyer
(74) *Attorney, Agent, or Firm* — Schwegman, Lundberg & Woessner, P.A.

(57) ABSTRACT

Disclosed herein are a novel dicarboxylic acid salt of N,N-dimethylimidodicarbonimidic diamide, a preparation method thereof and a pharmaceutical composition comprising the same. More specifically, disclosed herein are a novel dicarboxylic acid salt of N,N-dimethylimidodicarbonimidic diamide, a crystalline acid addition salt prepared by allowing N,N-dimethylimidodicarbonimidic diamide to react with a specific dicarboxylic acid, which has improved physical and chemical properties including solubility, stability, non-hygroscopicity and anti-adhesive properties, and low toxicity, and thus is very effective in the prevention and treatment of not only diabetes and its complications in patients with so-called metabolic syndromes, in which diabetes, obesity, hyperlipidemia, fatty liver, coronary artery disease, osteoporosis, polycystic ovary syndromes, etc. appear in combination, but also p53 gene-deficient cancers, muscular pain, muscle cytotoxicity and rhabdomyolysis, as well as a preparation method thereof and a pharmaceutical composition comprising the same.

4 Claims, 8 Drawing Sheets

DSC

N,N-DIMETHYL IMIDODICARBONIMIDIC DIAMIDE DICARBOXYLATE, METHOD FOR PRODUCING THE SAME AND PHARMACEUTICAL COMPOSITIONS COMPRISING THE SAME

CROSS REFERENCE TO RELATED APPLICATION

This application is a nationalization under 35 U.S.C. 371 of PCT/KR2008/005574, filed Sep. 19, 2008 and published as WO 2009/038396 A2 on Mar. 26, 2009, which application claims priority to and the benefit of Korean Patent Application No. 10-2007-0096527, filed Sep. 21, 2007; Korean Patent Application No. 10-2007-0096533, filed Sep. 21, 2007; and Korean Patent Application No 10-2008-0062806, filed Jun. 30, 2008, which applications and publication are incorporated herein by reference and made a part hereof.

TECHNICAL FIELD

The present invention relates to a novel dicarboxylic acid salt of N,N-dimethyl imidodicarbonimidic diamide, a preparation method thereof and a pharmaceutical composition comprising the same. More specifically, the present invention relates to a novel dicarboxylic acid salt of N,N-dimethyl imidodicarbonimidic diamide, a crystalline acid addition salt prepared by allowing N,N-dimethylimidodicarbonimidic diamide to react with a specific dicarboxylic acid, which has improved physical and chemical properties including solubility, stability, non-hygroscopicity, anti-adhesive properties etc., and low toxicity, and thus is very effective in the prevention and treatment of not only diabetes and its complications in patients with so-called metabolic syndromes, in which diabetes, obesity, hyperlipidemia, fatty liver, coronary artery disease, osteoporosis, polycystic ovary syndromes, etc. appear in combination, but also p53 gene-deficient cancers, muscular pain, muscle cytotoxicity and rhabdomyolysis, and relates to a preparation method thereof and a pharmaceutical composition comprising the same.

BACKGROUND ART

N,N-dimethyl imidodicarbonimidic diamide is a biguanide drug, the generic name of which is metformin. When this drug is administered to type 2 diabetic patients or glucose intolerant patients, it can exhibit blood glucose lowering action by controlling glucose formation in the liver and increasing glucose utilization in muscles and improve lipid metabolism, thus preventing the development and deterioration of diabetes complications and treating diabetes complications.

It can be seen in several papers that only metformin among oral anti-diabetic drugs is a first-choice drug. Particularly, it was proved that metformin has the effect of activating AMPK, and thus the propriety of clinical effects thereof was demonstrated. It was reported that AMPK is a key enzyme physiologically controlling metabolism of carbohydrate and lipid, and metformin is effective in normalizing high glucose level, improving the condition of lipid, normalizing amenorrhea, ovulation and pregnancy, treating fatty liver, and preventing and treating p53 gene-deficient cancers by activating said enzyme.

According to a report by the Abramson Cancer Center of the University of Pennsylvania, metformin, an AMPK activator, is effective for the prevention and treatment of p53 gene-deficient cancers [Monica Buzzai, et al. Systemic Treatment with the Antidiabetic Drug Metformin Selectively Impairs p53 gene-Deficient Tumor Cellgrowth, Cancer Res 2007; 67:(14); Jul. 15, 2007].

The free base form of metformin is pharmaceutically useful, but has low stability. For this reason, metformin is administered in the form of a pharmaceutically acceptable acid addition salt.

Korean Patent No. 90,479 discloses that metformin prepared in the form of a pharmaceutically acceptable salt must be able to satisfy the following four physical and chemical standards: (1) good solubility; (2) good stability; (3) non-hygroscopicity; (4) processability into a tablet formulation. However, it is very difficult that the pharmaceutically acceptable acid addition salt of metformin satisfies all the four standards.

Studies on acid addition salts other than metformin hydrochloride have been conducted before. CN 1962661A discloses the preparation of metformin folate using folic acid which is used as an anti-pernicious anemia factor. International Patent Publication No. WO 2005/033067 discloses metformin 1,2,6,7,8,8a-hexahydro-beta, gamma, 6-trihydroxy-2-methyl-8-[2s]-2-methyl-1-oxobutoxy]-, (beta R, gamma R,1S,2S,6S,8S,8aS)-1-naphthaleneheptanoic acid which is used to treat hyperlipidemia and hyperglycemia. U.S. Pat. No. 3,957,853 discloses metformin acetylsalicylate, and U.S. Pat. No. 4,028,402 discloses novel acid addition salts of biguanide compounds. U.S. Pat. No. 4,080,472 discloses metformin clofibrate for treating diabetes-related diseases, and U.S. Pat. No. 6,031,004 discloses a pharmaceutical composition comprising metformin fumarate, succinate and maleate and the use thereof. In addition, U.S. Pat. No. 4,835,184 discloses p-chlorophenoxy-acetic acid salt, and U.S. Pat. No. 3,903,141 discloses adamantane acid salt.

As described above, studies on acid addition salts of metformin have been constantly conducted, but only metformin hydrochloride has been approved for use as a drug to date and has been widely used as an agent for treating non-insulin dependent diabetes mellitus. The conventional dosage of metformin hydrochloride is not more than 2550 mg/day, and a tablet comprising 500 mg or 750 mg of metformin hydrochloride is administered at mealtime twice or three times a day. However, for pharmacological effects, such metformin hydrochloride and other acid addition salts must have improved physical and chemical properties, including improved solubility, stability, non-hygroscopicity and anti-adhesive properties, and reduced toxicity.

Meanwhile, studies on various pharmacological effects of malic acid have recently been actively conducted. Malic acid is in the form of white crystal or crystalline powder and has a slightly specific odor or is odorless. It is insoluble in ether, but well soluble in water and alcohol. It is involved in the Krebs cycle, the human metabolic process, and has excellent effects against arteriosclerosis or hypertension.

Studies on malic acid itself have been actively conducted, and the significant effects of malic acid as food have been reported. However, the effects of metformin malate as disclosed in the present invention have not been reported, and the interaction of malic acid with metformin has also not been reported.

Meanwhile, in a process of producing metformin in the form of a free base according to prior patents (U.S. Pat. No. 4,080,472), there is a problem in that the use of an ion-exchange resin column, or severe production conditions, including as the reflux of solvent by heating and the filtration of hot solution, are required to remove hydrochloric acid from metformin hydrochloride.

DISCLOSURE OF INVENTION

Technical Problem

It is an object of the present invention to provide a novel dicarboxylic acid salt of metformin, which is excellent in physical and chemical properties, including solubility, stability, non-hygroscopicity and anti-adhesive properties, and has low toxicity.

Another object of the present invention is to provide a method for preparing metformin dicarboxylate, which does not require severe production conditions, including the use of an ion-exchange resin column, the reflux of solvent by heating, and filtration in hot conditions.

Still another object of the present invention is to provide a pharmaceutical composition, which comprises a novel dicarboxylic acid salt of metformin as an active ingredient and is very effective in the prevention and treatment of not only diabetes and its complications in patients with metabolic syndromes, in which diabetes, obesity, hyperlipidemia, fatty liver, coronary artery disease, osteoporosis, polycystic ovary syndromes, etc. appear in combination, but also p53 gene-deficient cancers, muscular pain, muscle cytotoxicity and rhabdomyolysis.

Technical Solution

The present invention consists of the following elements (1)-(12).

(1) Metformin dicarboxylate represented by the following formula 1:

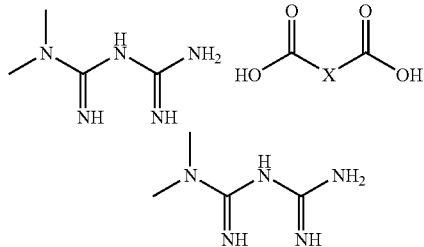

[Formula 1]

wherein X is —(CH$_2$)$_n$— (n=1, 3 or 4) or —CH$_2$—CH(OH)—.

(2) The metformin dicarboxylate of the above (1), which is in the form of anhydride or hydrate.

(3) A method for preparing metformin dicarboxylate represented by formula 1, which comprises allowing 2-4 molar equivalents of metformin hydrochloride of the following formula 2 to react with 2-4 molar equivalents of inorganic alkali in water, organic solvent or a mixture thereof to produce a metformin free-base of the following formula 3, and then allowing the metformin free-base to react with 1 molar equivalent of dicarboxylic acid of the following formula 4:

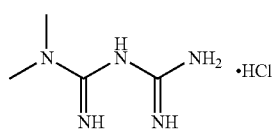

[Formula 2]

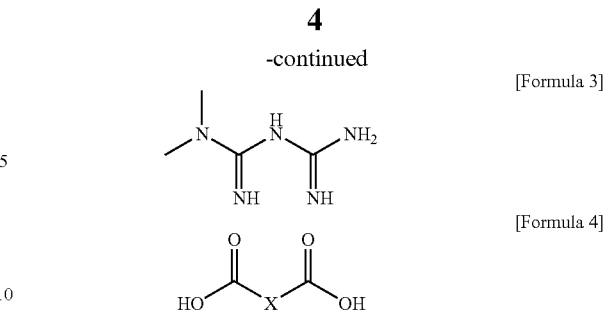

[Formula 3]

[Formula 4]

wherein X is —(CH$_2$)$_n$— (n=1, 3 or 4) or —CH$_2$—CH(OH)—.

(4) A method for preparing metformin malate of the following formula 1a, which comprises allowing 2-4 molar equivalents of metformin hydrochloride of the formula 2 to react with 2-4 molar equivalents of organic alkali and 1 molar equivalent of malic acid in organic solvent, simultaneously:

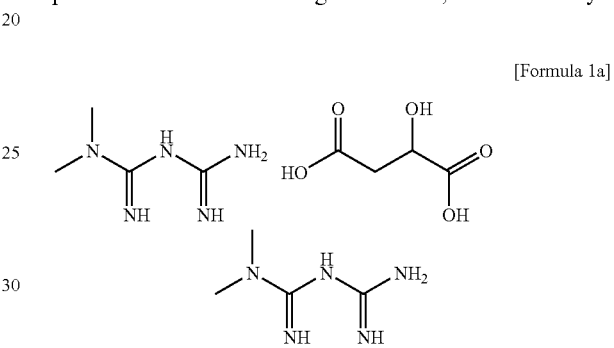

[Formula 1a]

(5) A method for preparing metformin malate represented by formula 1a, which comprises allowing 2-4 molar equivalents of metformin hydrochloride of the formula 2 to react with 1 molar equivalent of organic alkali of the following formula 5 in water:

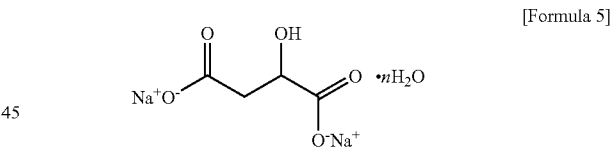

[Formula 5]

n = ½, 3

(6) The method of the above (3), which is metformin (2:1) malonate, metformin (2:1) glutarate, metformin (2:1) adipate, or metformin (2:1) malate.

(7) The method of the above (3), wherein the inorganic alkali is sodium hydroxide or potassium hydroxide.

(8) The method of the above (4), wherein the organic alkali is potassium carbonate.

(9) The method of the above (3) or (4), wherein the organic solvent comprises at least one selected from the group consisting of tetrahydrofuran, dimethylformamide, methanol, ethanol, isopropanol, acetone and acetonitrile.

(10) A pharmaceutical composition for preventing or treating at least one selected from the group consisting of diabetes and its complications in patients with metabolic syndromes, in which diabetes, obesity, hyperlipidemia, fatty liver, coronary artery disease, osteoporosis, and polycystic ovary syndromes appear in combination, p53 gene-deficient cancers, muscular pain, muscle cytotoxicity and rhabdomyolysis, wherein the composition comprises the metformin dicarboxylate of formula 1 as an active ingredient.

(11) The pharmaceutical composition of the above (10), which is in the form of a tablet or a capsule.

(12) The pharmaceutical composition of the above (10) or (11), which is orally administered at a dosage of 50-3,000 mg as metformin free-base over 1-3 times a day.

ADVANTAGEOUS EFFECTS

A novel dicarboxylic acid salt of metformin according to the present invention shows an excellent effect of lowering blood glucose compared to that of metformin hydrochloride which was used as an anti-diabetic drug in the prior art. Particularly, it is very effective in lowering blood glucose not only on an empty stomach, but also after a meal, and shows the effect of increasing insulin sensitivity.

Also, a method for preparing the novel dicarboxylic acid salt of metformin according to the present invention can be carried out in a simple manner without special equipment. According to the inventive method for preparing metformin dicarboxylate, a novel salt of metformin can be synthesized at lower cost through a simple and improved process in general production equipment without special equipment. Thus, the method of the present invention has high industrial applicability.

As described above, the novel dicarboxylic acid salt of metformin according to the present invention is a crystalline acid addition salt suitable for the preparation of pharmaceutical formulations. It is prepared using dicarboxylic acid having relatively low toxicity, and thus has not only improved physical and chemical properties including stability, non-hygroscopicity and anti-adhesive properties, but also low toxicity, compared to existing metformin hydrochloride prepared using hydrochloric acid. Thus, it can provide a pharmaceutical composition, which is very effective in the prevention and treatment of not only diabetes and its complications in patients with metabolic syndromes, in which high blood glucose levels, diabetes, obesity, hyperlipidemia, fatty liver, coronary artery disease, osteoporosis, polycystic ovary syndromes, etc. appear in combination, but also p53 gene-deficient cancers, muscular pain, muscle cytotoxicity and rhabdomyolysis. In addition, it may also show excellent pharmacological effects.

Table 1 below shows the comparison of oral toxicity between hydrochloric acid, which forms the crystalline acid addition salt of metformin hydrochloride, and malonic acid, glutaric acid, adipic acid and malic acid, which form the crystalline acid addition salt of metformin dicarboxylate.

TABLE 1

| acid | Administration route | Subject animal | Dosage |
| --- | --- | --- | --- |
| Hydrochloric acid | oral | rabbit | $LD_{50}$ 900 mg/kg |
| Malonic acid | oral | rat | $LD_{50}$ 1310 mg/kg |
| glutaric acid | oral | rat | $LD_{50}$ 6000 mg/kg |
| Adipic acid | oral | rat | $LD_{50}$ 11000 mg/kg |
| malic acid | oral | rat | $LD_{50}$ 1600 mg/kg |

$LD_{50}$: 50% lethal dose

As can be seen in Table 1 above, hydrochloric acid used to prepare the crystalline acid addition salt of metformin is toxic in itself, but dicarboxylic acid which is used in the present invention shows relatively low toxicity compared to hydrochloric acid.

BEST MODE

Figure 1:
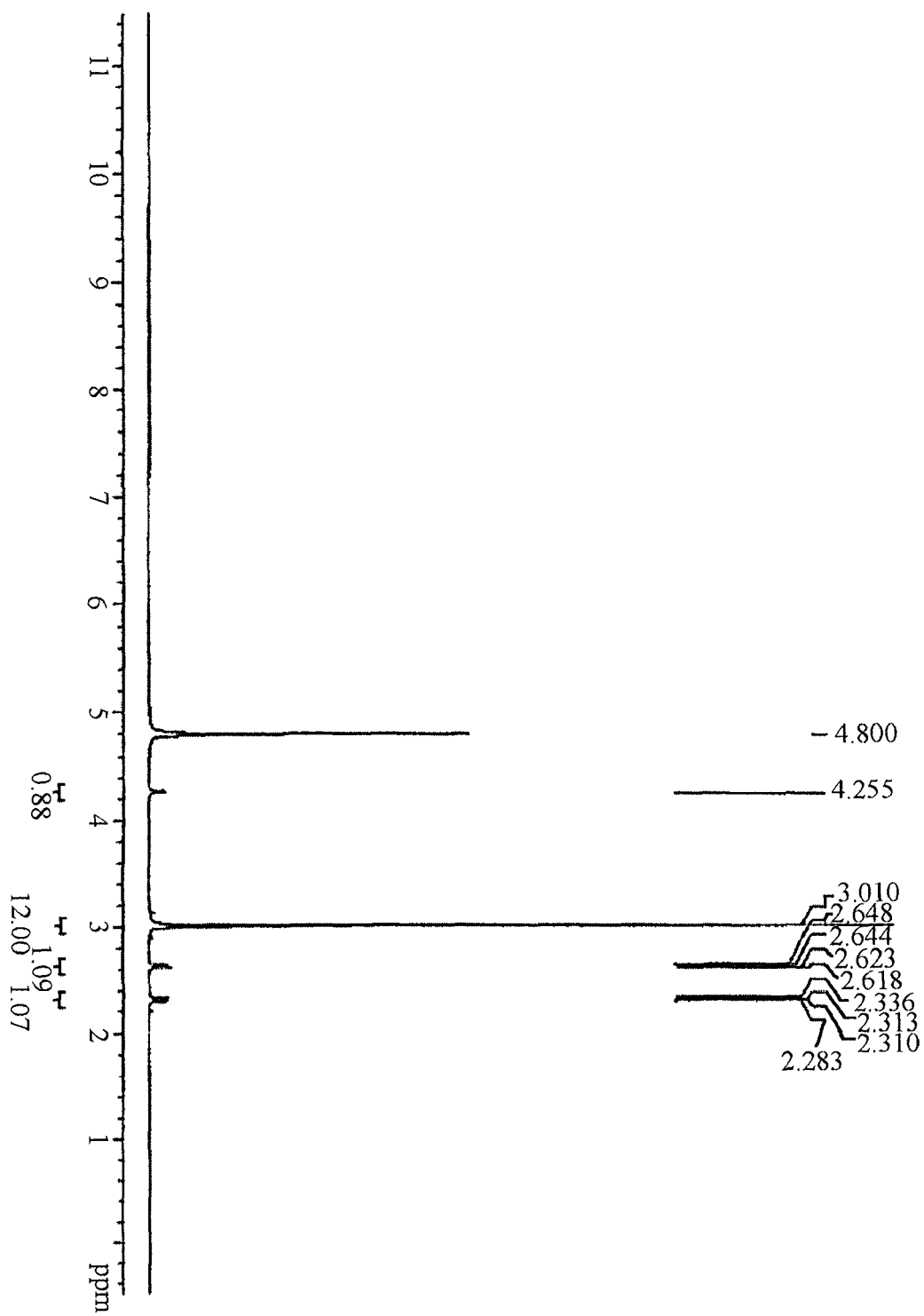
FIG. 1 shows the $^1$H-NMR spectrum of metformin malate, measured at 600 MHz (Varian-Inova 600).
Figure 2:
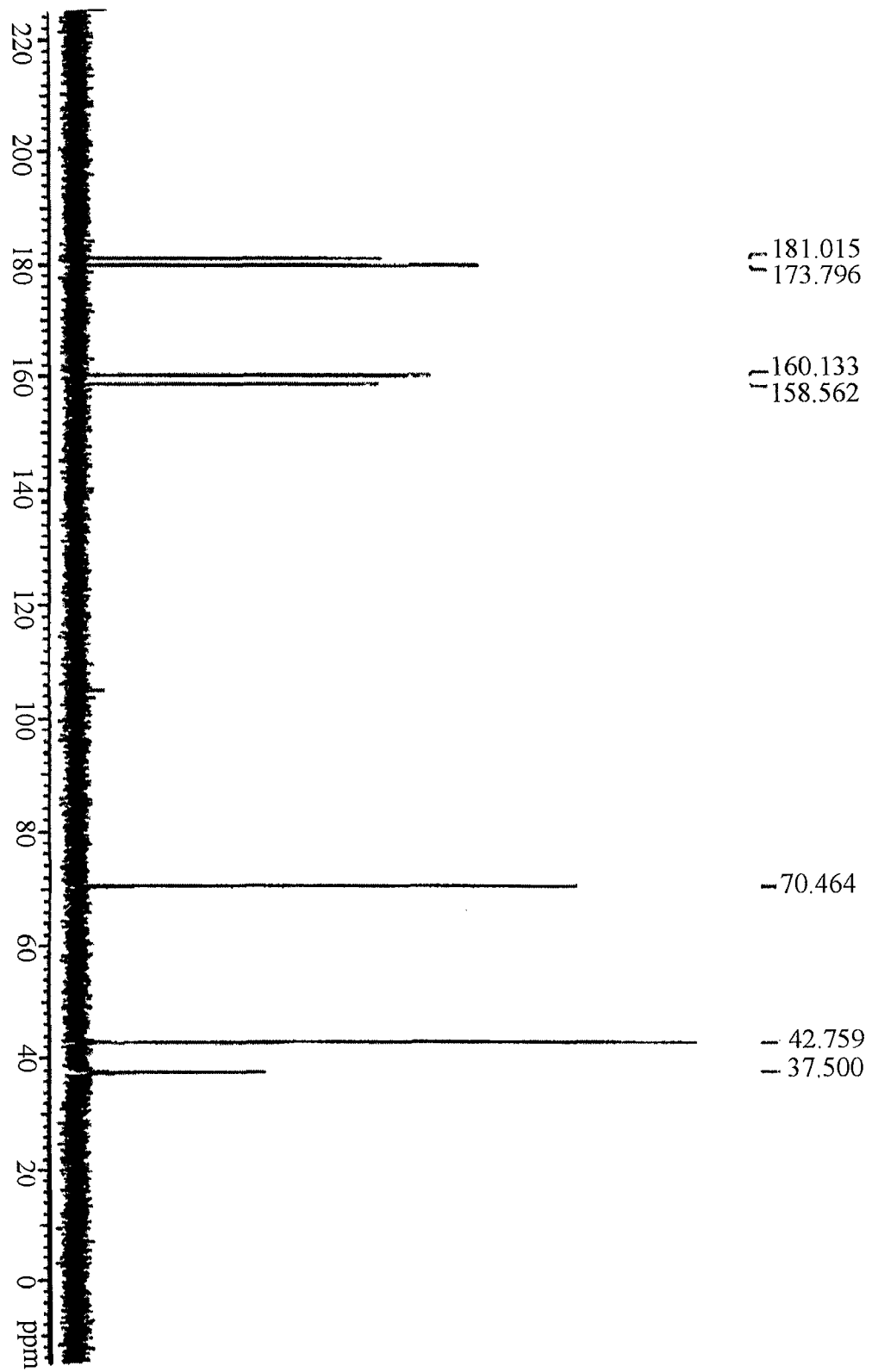
FIG. 2 shows the $^{13}$C-NMR spectrum of metformin malate, measured at 600 MHz (Varian-Inova 600).
Figure 3:
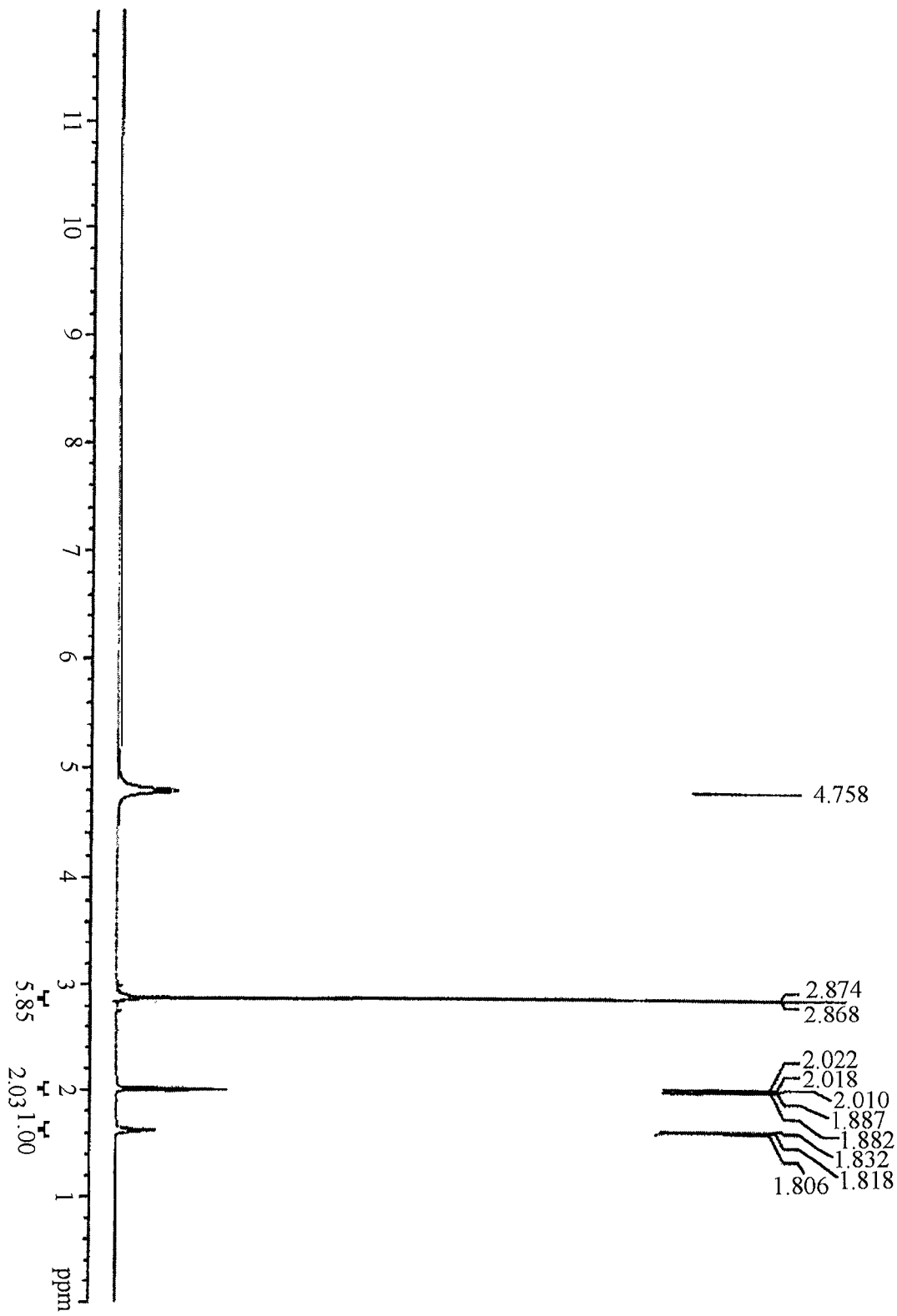
FIG. 3 shows the $^1$H-NMR spectrum of metformin glutarate, measured at 600 MHz (Varian-Inova 600).
Figure 4:
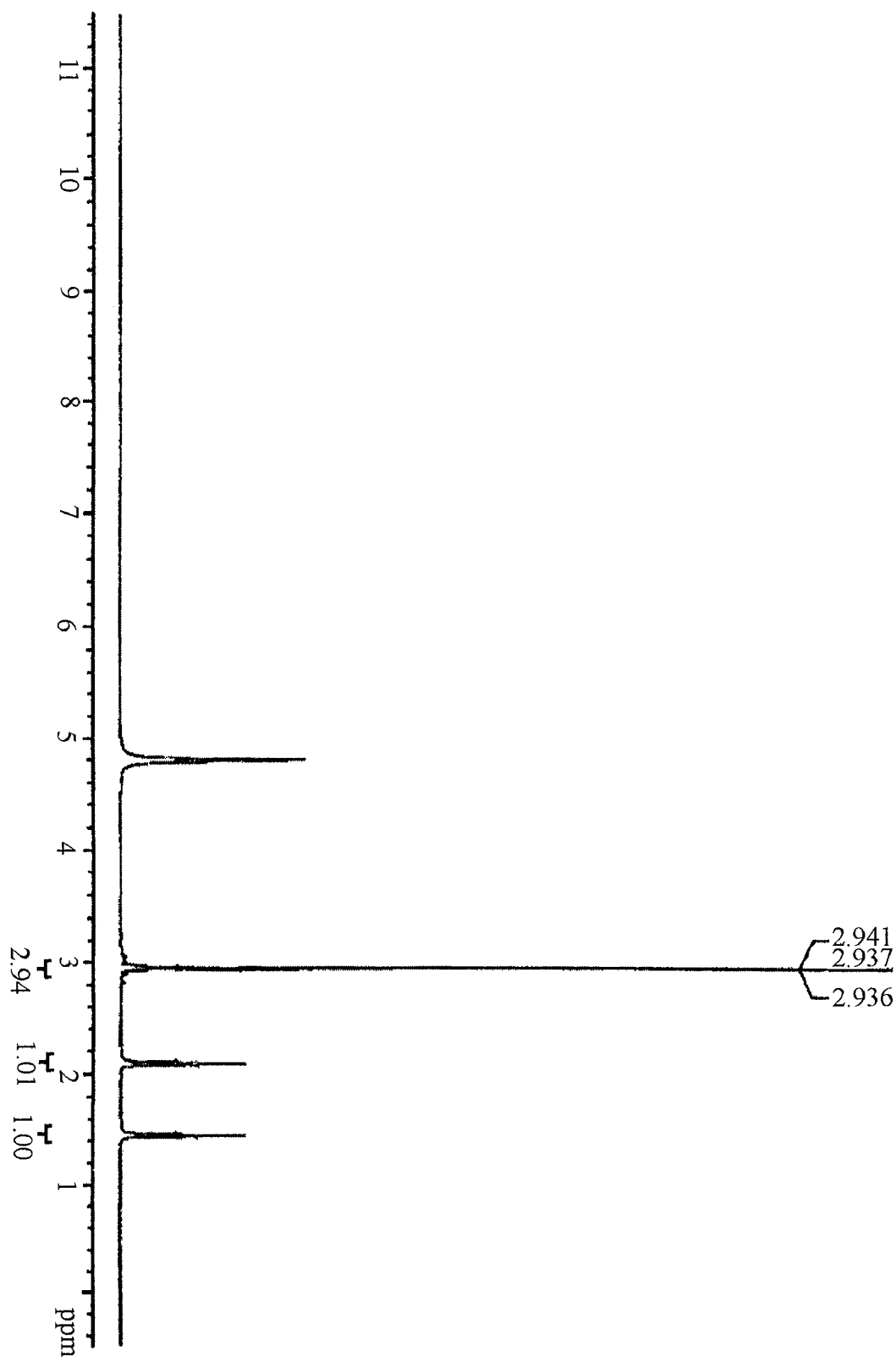
FIG. 4 shows the $^1$H-NMR spectrum of metformin adipate, measured at 600 MHz (Varian-Inova 600).

The present invention relates to a novel dicarboxylic acid salt of metformin of the following formula 1, which has excellent physical and chemical properties including solubility, stability, non-hygroscopicity and anti-adhesive properties, and low toxicity, and thus is particularly effective in preventing or treating diabetes or its complications.

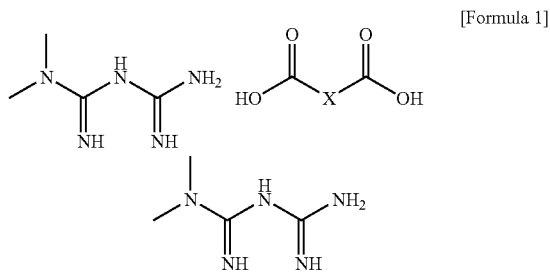

[Formula 1]

wherein X is —$(CH_2)_n$— (n=1, 3 or 4) or —$CH_2$—CH(OH)—.

The novel dicarboxylic acid salt of metformin of formula 1 according to the present invention is metformin malonate when X in formula 1 is —$(CH_2)$—, metformin glutarate when X is —$(CH_2)_3$—, metformin adipate when X is —$(CH_2)_4$—, and metformin malate when X is —$CH_2$—CH(OH)—.

Also, the present invention includes a method for preparing the metformin dicarboxylate of formula 1. As shown in the following reaction scheme 1, one embodiment of the preparation method comprises adding inorganic alkali to metformin hydrochloride of the following formula 2 in water, organic solvent or a mixture thereof to prepare a metformin free-base of the following formula 2, and then allowing the metformin free-base to react with dicarboxylic acid of the following formula 4:

[Reaction Scheme 1]

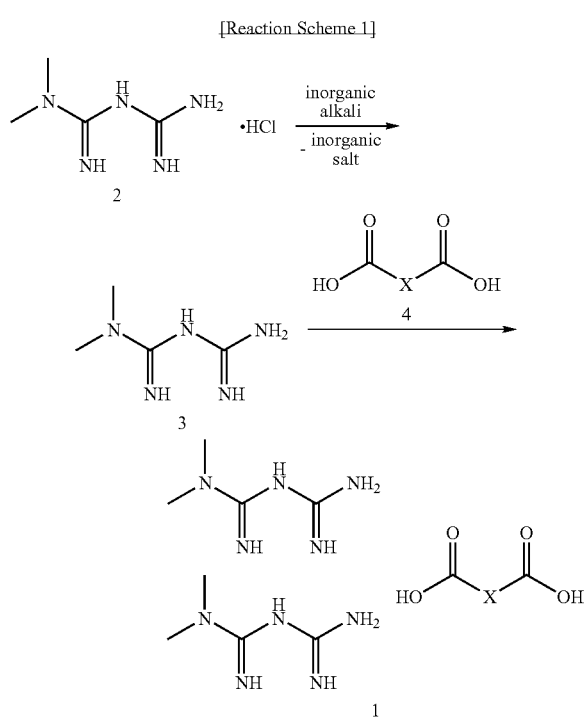

wherein X is —(CH$_2$)$_n$— (n=1, 3 or 4) or —CH$_2$—CH(OH)—.

The inventive preparation method as shown in reaction scheme 1 comprises the steps of:

1) allowing metformin hydrochloride of formula 2 to react with inorganic alkali in water, organic solvent or a mixture thereof to remove the addition salt;

2) dissolving dicarboxylic acid of formula 4 in organic solvent, and then adding the solution to the reaction solution comprising the metformin free-base of formula 3 to prepare a mixture; and 3) stirring the mixture, and filtering, washing and drying the obtained solid, thus forming a novel crystalline acid addition salt of formula 1.

The crystalline acid addition salt of metformin of formula 1 according to the present invention is prepared by adding dicarboxylic acid to the reaction solution comprising the metformin free-base of formula 3, and each step of the inventive preparation method will now be described in detail.

In step 1), sodium hydroxide, potassium hydroxide and the like may be used as the inorganic alkali. Preferably, sodium hydroxide is used. The inorganic alkali is preferably used in an amount of 2-4 molar equivalents relative to 2-4 molar equivalents of metformin hydrochloride.

In step 2), dicarboxylic acid is added to the reaction solution comprising the metformin free-base. The dicarboxylic acid is preferably used in an amount of 1 molar equivalent relative to 2-4 molar equivalents of the metformin free-base.

As the organic solvent in step 1) and step 2), at least one selected from the group consisting of tetrahydrofuran, dimethylformamide, methanol, ethanol, isopropanol, acetone and acetonitrile is preferably used.

Step 3) is a step of forming the crystalline acid addition salt. The reaction in step 3) is carried out at a temperature between −10° C. and 100° C.

In the present invention, metformin dicarboxylate may also be obtained through a more simplified process without carrying out the above steps 1) and 2). In this case, metformin dicarboxylate can be prepared by allowing metformin hydrochloride to react simultaneously with either organic alkali (such as potassium carbonate) or inorganic alkali (such as sodium hydroxide or potassium hydroxide) and dicarboxylic acid in organic solvent. Herein, the organic or inorganic alkali and the dicarboxylic acid are preferably used in amounts of 2-4 molar equivalents and 1 molar equivalent, respectively, relative to 2-4 molar equivalents of metformin malate. Metformin malate may also be prepared by allowing metformin hydrochloride to react in water with organic alkali comprising at least one selected from the group consisting of sodium malate, its semihydrate, its trihydrate, and mixtures thereof. Herein, the organic alkali is preferably used in an amount of 1 molar equivalent relative to 2-4 molar equivalents of metformin hydrochloride.

As used herein, the terms "metformin malonate", "metformin glutarate", "metformin adipate" and "metformin malate", unless specified otherwise, refer to metformin (2:1) malonate, metformin (2:1) glutarate, metformin (2:1) adipate, and metformin (2:1) malate, respectively.

In the present invention, metformin malonate, metformin glutarate, metformin adipate, and metformin malate include their all anhydrides and hydrates. The hydrate is preferably ¼ hydrate or trihydrate.

In the present invention, a process for preparing the metformin free-base was established such that it can be carried out without special equipment. In order to remove the hydrochloric acid of metformin hydrochloride, U.S. Pat. No. 4,080,472 discloses the use of an ion-exchange resin column, and U.S. Pat. No. 4,028,402 discloses a method of synthesis in severe production conditions, including the reflux of solvent by heating and the filtration of hot solution. However, in the present invention, the process was simplified such that organic salts of metformin can be synthesized at lower cost in general production equipment without special equipment. Thus, the present invention has high industrial applicability. This method for synthesizing free bases may also be used in reactions with various acids which are used to prepare pharmaceutically acceptable salts.

In another aspect, the present invention relates to a pharmaceutical composition for the prevention or treatment of diabetes and its complications in patients with so-called metabolic syndromes, in which diabetes, obesity, hyperlipidemia, fatty liver, coronary artery disease, osteoporosis, polycystic ovary syndromes, etc. appear in combination, p53 gene-deficient cancers, muscular pain, muscle cytotoxicity and rhabdomyolysis, the composition comprising the metformin dicarboxylate of formula 1 as an active ingredient and are being in the form of various formulations.

Metformin dicarboxylate prepared according to the above-described method can be combined with a pharmaceutically acceptable carrier, such that it can be prepared into pharmaceutical formulations for the prevention or treatment of disease conditions associated with diabetes, including tablets, soft capsules, hard capsules, pills, granules, powders, injections or solutions.

Herein, examples of the pharmaceutically acceptable carrier may include starch, microcrystalline cellulose, lactose, glucose, mannitol, light anhydrous silicic acid, alkaline earth metal salt, polyethyleneglycol, dicalcium phosphate and the like. Examples of binders may include starch, microcrystalline cellulose, highly dispersed silicon dioxide, mannitol, lactose, polyethyleneglycol, polyvinylpyrrolidone, hydroxypropyl methylcellulose, hydroxypropylcellulose, natural gum, synthetic gum, copovidone, gelatin and the like. Examples of disintegrates may include starches or modified starches, such as sodium starch glyconate, corn starch, potato starch or pre-gelatinized starch; clays such as bentonite, montmorillonite or beegum; celluloses, such as microcrystalline cellulose, hydroxypropylcellulose or carboxymethylcellulose; alginates such as sodium alginate or alginic acid; crosslinked celluloses such as sodium croscarmellose; crosslinked polymers such as crospovidone; and effervescent materials such as sodium bicarbonate or citric acid. Examples of lubricants may include talc, light anhydrous silicic acid, magnesium stearate and alkaline earth metal stearate type calcium, zinc, etc., lauryl sulfate, hydrogenated vegetable oil, sodium benzoate, sodium stearyl fumarate, glyceryl monostearate, polyethylene glycol 4000 and the like. Other pharmaceutically acceptable additives such as coloring agents or perfumery may be used.

As described above, metformin dicarboxylate may be used in the form of various oral preparations. The dosage of the inventive pharmaceutical composition to the human body may vary depending on the patient's age, sex, weight, nationality, health status and disease severity and may be administered in division depending on the determination of physicians.

Hereinafter, the present invention will be described in further detail. It is to be understood, however, that these examples are illustrative only, and the scope of the present invention is not limited thereto.

EXAMPLES

Example 1

Preparation of Metformin Malonate 200.0 g (4 molar equivalents) of metformin hydrochloride and 48.3 g (4 molar equivalents) of sodium hydroxide were stirred in a mixed solution of 1.8 L of acetone and 0.8 L of water at room temperature. Then, the produced inorganic salt was filtered, and a solution of 31.4 g (1 molar equivalent) of malonic acid in acetone-water was added dropwise to the filtered solution and stirred at room temperature. The produced crystal was filtered and dried in hot air, thus obtaining 105.2 g (yield: 96.2%) of metformin malonate.

Example 2

Preparation of Metformin Glutarate 20.00 g (4 molar equivalents) of metformin hydrochloride and 4.83 g (4 molar equivalents) of sodium hydroxide were stirred in a mixed solution of 180 ml of chloroform-methylalcohol (15:1) and 8 ml of water at room temperature, and then produced salt was filtered. To the filtered solution, a solution of 3.98 g (1 molar equivalent) of glutaric acid in chloroform-methylalcohol (15:1) was added dropwise and stirred at room temperature. The produced crystal was filtered and dried in hot air, thus obtaining 11.39 g (yield: 96.9%) of metformin glutarate.

Example 3

Preparation of Metformin Glutarate 40.0 g of metformin hydrochloride and 9.67 g of potassium hydroxide were stirred in a mixed solution of 180 ml of acetone and 8 ml of water at room temperature, and then the produced inorganic salt was filtered. To the filtered solution, a solution of 7.98 g of glutaric acid in acetone-water was added dropwise and stirred at room temperature. The produced crystal was filtered and dried in hot air, thus obtaining 16.7 g (yield: 70.8%) of metformin glutarate.

Example 4

Preparation of Metformin Glutarate (1) 10.0 g of metformin hydrochloride and 2.40 g of sodium hydroxide were stirred in 100 ml of ethylalcohol at a temperature of 70° C., and then methylene chloride was added thereto. The produced inorganic salt was filtered, and ethyl acetate was added thereto, thus preparing metformin free-base. The produced crystal was filtered and dried in hot air, thus obtaining 6.50 g (yield: 83.4%) of metformin free-base.

(2) 10.0 g of the metformin free-base and 3.98 g of glutaric acid were stirred in 100 ml of methyl alcohol at a temperature of 40° C., and then ethyl acetate was added thereto. The produced crystal was filtered and dried in hot air, thus obtaining 5.15 g (yield: 43.8%) of metformin glutarate.

Example 5

Preparation of Metformin Glutarate 10.0 g of metformin, 2.40 g of sodium hydroxide and 3.98 g of glutaric acid were stirred in 150 ml of ethyl alcohol at a temperature of 70° C., and then methylene chloride was added thereto. The produced inorganic salt was filtered and ethyl acetate was added to the filtered solution. The produced crystal was filtered and dried in hot air, thus obtaining 6.79 g (yield: 57.7%) of metformin glutarate.

Example 6

Preparation of Metformin Glutarate 20 g (4 molar equivalents) of metformin hydrochloride and 4.83 g (4 molar equivalents) of sodium hydroxide were stirred in a mixed solution of 180 ml of acetonitrile and 8 ml of water at room temperature, and then the produced inorganic salt was filtered. To the filtered solution, a solution of 3.98 g (1 molar equivalent) of glutaric acid in acetonitrile-water was added dropwise and stirred at room temperature. The produced crystal was filtered and dried in hot air, thus obtaining 6.24 g (yield: 52.9%) of metformin glutarate.

Example 7

Preparation of Metformin Glutarate 20 g (4 molar equivalents) of metformin hydrochloride and 4.83 g (4 molar equivalents) of sodium hydroxide were stirred in a mixed solution of 180 ml of acetonitrile and 8 ml of water at room temperature, and then the produced inorganic salt was filtered. To the filtered solution, a solution of 3.98 g (1 molar equivalent) of glutaric acid in acetonitrile-water was added dropwise and stirred at 10° C. The produced crystal was filtered and dried in hot air, thus obtaining 5.8 g (yield: 49.1%) of metformin glutarate.

Example 8

Preparation of Metformin Glutarate 12.5 g (2.5 molar equivalents) of metformin hydrochloride and 3.02 g (2.5 molar equivalents) of sodium hydroxide were stirred in a mixed solution of 112.5 ml of acetone and 5 ml of water at room temperature, and then the produced inorganic salt was filtered. To the filtered solution, 3.98 g (1 molar equivalent) of glutaric acid in acetone-water was added dropwise and stirred at room temperature. The produced crystal was filtered and dried in hot air, thus obtaining 11.12 g (yield: 94.3%) of metformin glutarate.

Example 9

Preparation of Metformin Glutarate 12.5 g (2.5 molar equivalents) of metformin hydrochloride and 3.02 g (2.5 molar equivalents) of sodium hydroxide were stirred in a mixed solution of 112.5 ml of acetone and 5 ml of water at room temperature, and then the produced inorganic salt was filtered. To the filtered solution, a solution of 3.98 g (1 molar equivalent) of glutaric acid in acetone-water was added dropwise and stirred at 10° C. The produced crystal was filtered and dried in hot air, thus 10.88 g (yield: 92.2%) of metformin glutarate.

Example 10

Preparation of Metformin Glutarate 12.5 g (2.5 molar equivalents) of metformin hydrochloride and 3.02 g (2.5 molar equivalents) of sodium hydroxide were stirred in a mixed solution of 56.25 ml of acetone and 5 ml of water, and then the produced inorganic salt was filtered. To the filtered solution, a solution of 3.98 g (1 molar equivalent) of glutaric acid in acetone-water was added dropwise and stirred at 10° C. The produced crystal was filtered and dried in hot air, thus obtaining 10.47 g (yield: 88.8%) of metformin glutarate.

Example 11

Preparation of Metformin Glutarate 12.5 g (2.5 molar equivalents) of metformin hydrochloride and 3.02 g (2.5 molar equivalents) of sodium hydroxide were stirred in a mixed solution of 112.5 ml of tetrahydrofuran (THF) and 5 ml of water at room temperature, and then the produced inorganic salt was filtered. To the filtered solution, a solution of 3.98 g (1 molar equivalent) of glutaric acid in tetrahydrofuran-water was added dropwise and stirred at 10° C. The produced crystal was filtered and dried in hot air, thus obtaining 11.41 g (yield: 96.7%) of metformin glutarate.

Example 12

Preparation of Metformin Glutarate 9.97 g (2 molar equivalents) of metformin hydrochloride and 3.38 g (2 molar equivalents) were stirred in 180 ml of ethanol at 40° C., and then the produced inorganic salt was filtered. To the filtered solution, a solution of 3.98 g (1 molar equivalent) of glutaric acid in ethanol was added dropwise and stirred at 10° C., and then the produced crystal was filtered. The produced crystal was stirred in ethanol at 50° C., and then stirred at 10° C. for 5 hours. Then, the stirred solution was dried in hot air, thus obtaining 7.27 g (yield: 61.6%) of metformin glutarate.

Example 13

Preparation of Metformin Glutarate (1) 500 g (1 molar equivalent) of metformin hydrochloride and 120.76 g (1 molar equivalent) of sodium hydroxide were stirred in 3750 ml of methanol at room temperature, the produced inorganic salt was filtered, and the filtrate was concentrated. The produced crystal was stirred in 5000 ml of acetone at 40° C., the produced inorganic salt was filtrated, and the filtrate was concentrated. The produced crystal was stirred in 4000 ml of acetone at 40° C., the produced inorganic salt was filtered, and the filtrate was concentrated, thus obtaining 233.3 g (yield: 59.84%) of metformin free-base.

(2) 9.75 g (2.5 molar equivalents) of the metformin free-base was stirred in a mixed solution of 112.5 ml of acetone and 5 ml of water at 40° C., and a solution of 3.98 g (1 molar equivalent) of glutaric acid in acetone-water was added dropwise thereto and stirred at 10° C. The produced crystal was filtered and dried in hot air, thus obtaining 11.24 g (yield: 95.3%) of metformin glutarate.

Example 14

Preparation of Metformin Glutarate 9.75 g (2.5 molar equivalents) of metformin free-base was stirred in 100 ml of ethanol at room temperature, after which a solution of 3.98 g (1 molar equivalent) of glutaric acid in ethanol was added dropwise thereto and stirred at 10° C. The produced crystal was filtered and dried in hot air, thus obtaining 7.41 g (yield: 62.8%) of metformin glutarate.

Example 15

Preparation of Metformin Adipate 20.0 g of metformin hydrochloride and 4.83 g of sodium hydroxide were stirred in a mixed solution of 180 ml of acetone and 8 ml of water at room temperature, and then the produced inorganic salt was filtered. To the filtered solution, a solution of 4.41 g of adipic acid in acetone-water was added dropwise and stirred at room temperature. The produced crystal was filtered and dried in hot air, thus obtaining 11.26 g (yield: 92.3%) of metformin adipate.

Example 16

Preparation of Metformin Adipate 40.0 g of metformin hydrochloride and 9.66 g of potassium hydroxide were stirred in a mixed solution of 360 ml of acetone and 16 ml of water at room temperature, and then the produced inorganic salt was filtered. To the filtered solution, a solution of 8.82 g of adipic acid in acetone-water was added dropwise and stirred at room temperature. The produced crystal was filtered and dried in hot air, thus obtaining 22.01 g (yield: 90.2%) of metformin adipate.

Example 17

Preparation of Metformin Adipate (1) 10.00 g of metformin hydrochloride and 2.40 g of sodium hydroxide were stirred in 100 ml of ethyl alcohol at 70° C., and the produced inorganic salt was filtered. Then, ethyl acetate was added thereto, thus preparing metformin free-base. The produced crystal was filtered and dried in hot air, thus obtaining 6.50 g (yield: 83.4%) of metformin free-base.

(2) 10.00 g of the metformin free-base and 4.411 g of adipic acid were stirred in 150 ml of methyl alcohol at 40° C., and then ethyl acetate was added thereto. The produced crystal was filtered and dried in hot air, thus obtaining 12.06 g (yield: 98.9%) of metformin adipate.

Example 18

Preparation of Metformin Adipate 10.00 g of metformin hydrochloride, 2.40 g of sodium hydroxide and 2.20 g of adipic acid were stirred in 150 ml of ethyl alcohol at 70° C., and then methylene chloride was added thereto. Then, the produced inorganic salt was filtered, and ethyl acetate was added to the filtrate. The produced crystal was filtered and dried in hot air, thus obtaining 4.90 g (yield: 80.5%) of metformin adipate.

Example 19

Preparation of Metformin Adipate (1) 20 g (4 molar equivalents) of metformin hydrochloride and 4.83 g (4 molar equivalents) of sodium hydroxide were stirred in a mixed solution of 180 ml of acetonitrile and 8 ml of water at room temperature, and then the produced inorganic salt was filtered. To the filtered solution, a solution of 4.41 g (1 molar equivalent) of adipic acid in acetonitrile-water was added dropwise and stirred at room temperature. The produced crystal was filtered and dried in hot air, thus obtaining 12.63 g (yield: 103.43%) of metformin adipate.

(2) 10 g (1 molar equivalent) of metformin adipate was stirred in ethanol at 50° C., and then stirred at 10° C. for 5 hours. Then, the produced crystal was filtered and dried in hot air, thus obtaining 5.92 g (yield: 59.2%) of metformin adipate.

Example 20

Preparation of Metformin Adipate 12.5 g (2.5 molar equivalents) of metformin hydrochloride and 3.02 g (2.5 molar equivalents) of sodium hydroxide were stirred in a mixed solution of 112.5 ml of acetone and 5 ml of water at room temperature, and then the produced inorganic salt was filtered. To the filtered solution, a solution of 4.41 g (1 molar equivalent) of adipic acid in acetone-water was added dropwise and stirred at room temperature. The produced crystal was filtered and dried in hot air, thus obtaining 10.95 g (yield: 89.6%) of metformin adipate.

Example 21

Preparation of Metformin Adipate (1) 12.5 g (2.5 molar equivalents) of metformin hydrochloride and 3.02 g (2.5 molar equivalents) of sodium hydroxide were stirred in a mixed solution of 112.5 ml of tetrahydrofuran (THF) and 5 ml of water at room temperature, and then the produced inorganic salt was filtered. To the filtered solution, a solution of 4.41 g (1 molar equivalent) of adipic acid in tetrahydrofuran (THF)-water was added dropwise and stirred at room temperature. The produced crystal was filtered and dried in hot air, thus obtaining 11.94 g (yield: 97.7%) of metformin adipate.

(2) 8.12 g (1 molar equivalent) of metformin adipate was stirred in ethanol at 50° C., and then stirred at 10° C. for 5 hours. Then, the produced crystal was filtered and dried in hot air, thus obtaining 6.7 g (yield: 82.5%) of metformin adipate.

Example 22

Preparation of Metformin Adipate (1) 500 g (1 molar equivalent) of metformin hydrochloride and 120.76 g (1 molar equivalent) of sodium hydroxide were stirred in 3750 ml of methanol at room temperature, after which the produced inorganic salt was filtered, and the filtrate was concentrated. The produced crystal was stirred in 5000 ml of acetone at 40° C., and then the produced inorganic salt was filtrated, and the filtrate was concentrated. The produced crystal was stirred in 4000 ml of acetone at 40° C., and then the produced crystal was filtrated, and the filtrate was concentrated, thus obtaining 233.3 g (yield: 59.84%) of metformin free-base.

(2) 9.75 g (2.5 molar equivalents) of the metformin free-base was stirred in a mixed solution of 112.5 ml of acetone and 5 ml of water at 40° C., and then a solution of 4.41 g (1 molar equivalent) of adipic acid in acetone-water was added dropwise thereto and stirred at room temperature. The produced crystal was filtered and dried in hot air, thus obtaining 11.47 g (yield: 93.9%) of metformin adipate.

Example 23

Preparation of Metformin Malate 12.5 g (2.5 molar equivalents) of metformin hydrochloride and 3.02 g (2.5 molar equivalents) of sodium hydroxide were stirred in a mixed solution of 112.5 ml of acetone and 5 ml of water at room temperature, and then the produced inorganic salt was filtered. To the filtered solution, a solution of 4.05 g (1 molar equivalent) of malate in acetone-water was added dropwise and stirred at room temperature. The produced crystal was filtered and dried in hot air, thus obtaining 11.83 g (yield: 99.8%) of metformin malate.

Example 24

Preparation of Metformin Malate 20.0 g (4 molar equivalents) of metformin hydrochloride and 4.83 g (4 molar equivalents) of sodium hydroxide were stirred in a mixed solution of 180 ml of tetrahydrofuran and 8 ml of water at room temperature, and then the produced inorganic salt was filtered. To the filtered solution, a solution of 4.05 g (1 molar equivalent) of malic acid in acetone-water was added dropwise and stirred at room temperature. The produced crystal was filtered and dried in hot air, thus obtaining 11.85 g (yield: 100%) of metformin malate.

Example 25

Preparation of Metformin Malate 12.5 g (2.5 molar equivalents) of metformin hydrochloride, 3.02 g (2.5 molar equivalents) of sodium hydroxide and 4.05 g (1 molar equivalent) of malic acid were stirred in a mixed solution of methanol and ethanol (1:1) at 40° C., and then the produced crystal was filtered. The produced crystal was stirred in ethanol at 50, and the stirred at 10° C. for 5 hours. Then, the crystal was filtered and dried in hot air, thus obtaining 8.94 g (yield: 75.4%) of metformin malate.

Example 26

Preparation of Metformin Malate 9.97 g (2 molar equivalents) of metformin hydrochloride and 3.38 g (2 molar equivalents) of potassium hydroxide were stirred in 180 ml of ethanol at 40° C., then the produced inorganic salt was filtered. To the filtered solution, a solution of 4.05 g (1 molar equivalent) of malic acid in ethanol was added dropwise and stirred at room temperature, and the produced crystal was filtered. The produced crystal was stirred in ethanol at 50° C., and then stirred at 10° C. for 5 hours. Then, the produced crystal was filtered and dried in hot air, thus obtaining 9.92 g (yield: 83.7%) of metformin malate.

Example 27

Preparation of Metformin Malate 9.97 g (2 molar equivalents) of metformin hydrochloride, 8.34 g (2 molar equivalents) of potassium carbonate and 4.05 g (1 molar equivalent) of malate were stirred in N,N-dimethylformamide (DMF) at 100° C., and then the produced inorganic salt was filtered. To the filtered solution, acetone was added dropwise and stirred at room temperature. The produced crystal was filtered and dried in hot air, thus obtaining 1.49 g (yield: 12.6%) of metformin malate.

Example 28

Preparation of Metformin Malate 20 g (4 molar equivalents) of metformin hydrochloride and 4.83 g (4 molar equivalents) of sodium hydroxide were stirred in a mixed solution of 180 ml of acetonitrile and 8 ml of water at room temperature, and then the produced inorganic salt was filtered. To the filtered solution, a solution of 4.05 g (1 molar equivalent) of malic acid in acetonitrile-water was added dropwise and stirred at room temperature. The produced crystal was filtered and dried in hot air, thus obtaining 11.85 g (yield: 100%) of metformin malate.

Example 29

Preparation of Metformin Malate 12.5 g (2.5 molar equivalents) of metformin hydrochloride and 3.02 g (2.5 molar equivalents) of sodium hydroxide were stirred in a mixed solution of 180 ml of methanol and 8 ml of water at room temperature, and then the produced inorganic salt was filtered. To the filtered solution, a solution of 4.05 g (1 molar equivalent) of malic acid in methanol-water was added dropwise and stirred at room temperature. The produced crystal was filtered and dried in hot air, thus obtaining 9.27 g (yield: 78.2%) of metformin malate.

Example 30

Preparation of Metformin Malate 12.5 g (2.5 molar equivalents) of metformin hydrochloride and 3.02 g (2.5 molar equivalents) of sodium hydroxide were stirred in a mixed solution of 56.25 ml of acetone and 5 ml of water at room temperature, and the produced inorganic salt was filtered. To the filtered solution, a solution of 4.05 g (1 molar equivalent) of malic acid in acetone-water was added dropwise and stirred at room temperature. The produced crystal was filtered and dried in hot air, thus obtaining 11.64 g (yield: 98.2%) of metformin malate.

Example 31

Preparation of Metformin Malate 20 g (2 molar equivalents) of metformin hydrochloride and 11.3 g (1 molar equivalent) of sodium malate semihydrate were stirred in 70 ml of water at 100° C., and then acetone was added dropwise thereto at less than 10° C. Then, the produced crystal was stirred for 1 hour, filtered and dried in hot air, thus obtaining 14.29 g (yield: 60.4%) of metformin malate.

Example 32

Preparation of Metformin Malate 20 g (2 molar equivalents) of metformin hydrochloride, 4.83 g (2 molar equivalents) of sodium hydroxide and 8.09 g (1 molar equivalent) of malic acid were stirred in 90 ml of water at 100° C., and acetone was added dropwise thereto at room temperature. Then, the produced crystal was stirred at room temperature for 1 hour, filtered and dried in hot air, thus obtaining 10.69 g (yield: 45.1%) of metformin malate.

Example 33

Preparation of Metformin Malonate-comprising Tablet 547.1 g of metformin malonate and 97.9 g of microcrystalline cellulose (Avicel PH102, FMC Biopolymer, USA) were sieved through sieve No. 20 and then mixed with each other in a drum mixer for 60 minutes. Meanwhile, 15 g of hydroxypropylcellulose (Klucel, Hercules, USA) and 5 g of colloidal silicon dioxide (Aerosil 200 VV, Degussa, Germany) were sieved through sieve No. 35, and the sieved material was added to and mixed with the mixture for 60 minutes. Finally, the 5 g of stearic acid was sieved through sieve No. 35 and added to and mixed with the mixture for 3 minutes.

Then, the final mixture powder was compressed into a tablet in a tablet press (GRC-15S, Sejong Pharmatech Co., Ltd., Korea) to prepare a tablet layer comprising 547.1 mg of metformin malonate per tablet. A coating layer was formed on the tablet layer using Opadry OY-C-7000A as a coating base in a Hi-coater (SFC-30N, Sejong Pharmatech Co., Ltd.), thus preparing a metformin malonate-comprising tablet.

Example 34

Preparation of Metformin Malonate-comprising Sustained-release Tablet 547.1 g of metformin malonate and 407.9 g of hydroxypropylmethylcellulose 2208 (Methocel K100M CR, Dow Chemical, USA) were sieved through sieve No. 20, and then mixed with each other in a mixer for 60 minutes. Meanwhile, 25 g of polyvinylpyrrolidone (Povidone, BASF, Germany) and 10 g of colloidal silicon dioxide (Aerosil 200 VV, Degussa, Germany) were sieved through sieve No. 35, and the sieved material was added to and mixed with the mixture for 60 minutes. Finally, 10 g of stearic acid was sieved through sieve No. 35 and added to and mixed with the mixture for 3 minutes.

Then, the final mixture powder was compressed into a tablet in a tablet press (GRC-15S, Sejong Pharmatech Co., Ltd., Korea) to prepare a sustained-release tablet layer comprising 547.1 mg of metformin malonate per tablet. A coating layer was formed on the tablet layer using Opadry OY-C-7000A as a coating base in a Hi-coater (SFC-30N, Sejong Pharmatech Co., Ltd.), thus preparing a metformin malonate-comprising sustained-release tablet.

Example 35

Preparation of Metformin Glutarate-comprising Tablet 589.4 g of metformin glutarate and 50.6 g of dicalcium phosphate were sieved through sieve No. 20 and then mixed with each other in a high-speed mixer for 3 minutes. Meanwhile, 20 g of polyvinylpyrrolidone (Povidone, BASF, Germany) was added to and dissolved in 120 g of isopropanol to prepare a binder solution. The binder solution was added to the high-speed mixer, and then the mixture was kneaded for 3 minutes. The kneaded material was dried in a steam dryer and then sieved through sieve No. 20. 10 g of colloidal silicon dioxide (Aerosil 200 VV, Degussa, Germany) was sieved through sieve No. 35, and the sieved material was added to and mixed with the mixture in a V-type mixer for 60 minutes. Finally, 6 g of stearic acid was sieved through sieve No. 35, and the sieved material was added to and mixed with the mixture for 3 minutes.

Then, the final mixture powder was compressed into a tablet in a tablet press (GRC-15S, Sejong Pharmatech Co., Ltd., Korea) to prepare a tablet layer comprising 589.4 mg of metformin glutarate per tablet. A coating layer was formed on the tablet layer using Opadry OY-C-7000A as a coating base in a Hi-coater (SFC-30N, Sejong Pharmatech Co., Ltd.), thus preparing a metformin glutarate-comprising tablet.

Example 36

Preparation of Metformin Glutarate-comprising Sustained-release Tablet 589.4 g of metformin glutarate and 370.6 g of polyethyleneoxide (Polyox Coagulant, Dow Chemical, USA) were sieved through sieve No. 20 and then mixed with each other in a V-type mixer for 60 minutes. Meanwhile, 25 g of hydroxypropylcellulose (Klucel, Hercules, USA) and 10 g of colloidal silicon dioxide (Aerosil 200 VV, Degussa, Germany) were sieved through sieve No. 35, and the sieved materials were added to and mixed with the mixture for 60 minutes. Finally, 10 g of magnesium stearate was sieved through sieve No. 35, and the sieved material was added to and mixed with the mixture for 3 minutes.

Then, the final mixture powder was compressed into a tablet in a tablet press (GRC-15S, Sejong Pharmatech Co., Ltd., Korea) to prepare a sustained-release tablet layer comprising 589.4 mg of metformin glutarate per tablet. A coating layer was formed on the tablet layer using Opadry OY-C-7000A as a coating base in a Hi-coater (SFC-30N, Sejong Pharmatech Co., Ltd.), thus preparing a metformin glutarate-comprising sustained-release tablet.

Example 37

Preparation of Metformin Adipate-comprising Capsule 305.27 g of metformin adipate and 1134.73 g of microcrystalline cellulose (Avicel PH102, FMC Biopolymer, USA) were sieved through sieve No. 20 and then mixed with each other in a V-type mixer for 60 minutes. 5 g of colloidal silicon dioxide (Aerosil 200 VV, Degussa, Germany) was sieved through sieve No. 35, and the sieved material was added to and mixed with the mixture for 60 minutes. Finally, 5 g of stearic acid was sieved through sieve No. 35, and the sieved material was added to and mixed with the mixture for 3 minutes.

Then, the final mixture powder was filled in a capsule in a capsule filling machine (SF-40N, Sejong Pharmatech, Korea), thus preparing a capsule comprising 305.27 mg of metformin adipate per capsule.

Example 38

Preparation of Metformin Adipate-comprising Released-release Tablet 610.54 g of metformin adipate and 374.46 g of hydroxypropylmethylcellulose 2208 (Methocel K100M CR, Dow Chemical, USA) were sieved through sieve No. 20 and mixed with each other in a double-cone mixer for 60 minutes. The mixed powder was compacted through rollers (VPS-1920, Poong-sung EIM, Korea) at a pressure of 15-25 Mpa to prepare slugs which were then sieved through sieve No. 20. Meanwhile, 15 g of hydroxypropylcellulose (Klucel, Hercules, USA) and 5 g of colloidal silicon dioxide (Aerosil 200 VV, Degussa, Germany) were sieved through sieve No. 35, and they were added to and mixed with the above-sieved material for 60 minutes. Finally, 10 g of magnesium stearate was sieved through sieve No. 35, and the sieved material was added to and mixed with the mixture for 3 minutes.

Then, the final mixture powder was compressed into a tablet in a tablet press (GRC-15S, Sejong Pharmatech Co., Ltd., Korea) to prepare a sustained-release tablet layer comprising 610.54 mg of metformin adipate per tablet. A coating layer was formed on the tablet layer using Opadry OY-C-7000A as a coating base in a Hi-coater (SFC-30N, Sejong Pharmatech Co., Ltd.), thus preparing a metformin adipate-comprising sustained-release tablet.

Example 39

Preparation of Metformin Malate-comprising Tablet 610.54 g of metformin malate and 28.46 g of microcrystalline cellulose (Avicel PH102, FMC Biopolymer, USA) were sieved through sieve No. 20 and then mixed with each other in a V-type mixer for 60 minutes. Meanwhile, 13 g of polyvinylpyrrolidone/polyvinylacetate (Kollidon VA64, BASF, Germany) and 4 g of colloidal silicon dioxide (Aerosil 200 VV, Degussa, Germany) were sieved through sieve No. 35, and the sieved materials were added to and mixed with the mixture for 60 minutes. Finally, 4 g of stearic acid was sieved through sieve No. 35, and the sieved material was added to and mixed with the mixture for 3 minutes.

Then, the final mixture powder was compressed into a tablet in a tablet press (GRC-15S, Sejong Pharmatech Co., Ltd., Korea) to prepare a tablet layer comprising 610.54 mg of metformin malate per tablet. A coating layer was formed on the tablet layer using Opadry OY-C-7000A as a coating base in a Hi-coater (SFC-30N, Sejong Pharmatech Co., Ltd.), thus preparing a metformin malate-comprising tablet.

Example 40

Preparation of Metformin Malate-comprising Film-coated Tablet 610.54 g of metformin malate and 300.46 g of hydroxypropylmethylcellulose 2208 (Methocel K100M CR, Dow Chemical, USA) were sieved through sieve No. 20 and then mixed with each other in a double-cone mixer for 60 minutes. Meanwhile, 12 g of hydroxypropylcellulose (Klucel, Hercules, USA) and 10 g of colloidal silicon dioxide (Aerosil 200 VV, Degussa, Germany) were sieved through sieve No. 35, and the sieved materials were added to and mixed with the mixture for 60 minutes. Finally, 7 g of stearic acid was sieved through sieve No. 35, and the sieved material was added to and mixed with the mixture for 3 minutes.

Then, the final mixture powder was compressed into a tablet in a tablet press (GRC-15S, Sejong Pharmatech Co., Ltd., Korea) to prepare a sustained-release tablet layer comprising 610.54 mg of metformin malate per tablet. A coating layer was formed on the tablet layer using Opadry OY-C-7000A as a coating base in an amount of 3 wt % to the weight of the uncoated tablet in a Hi-coater (SFC-30N, Sejong Pharmatech Co., Ltd.), thus preparing a metformin malate-comprising film-coated tablet.

Experimental Example 1

Powder X-ray Diffraction Spectrum

To measure the diffraction pattern of crystal structures, the plane distance of the crystals and the intensity of diffraction rays, powder X-ray diffraction analysis was carried out.

Characteristic peaks appearing in the powder X-ray diffraction spectra of metformin malonate, metformin glutarate, metformin adipate and metformin malate synthesized in Examples 1, 2, 15 and 23, respectively, are shown in Tables 2, 3, 4 and 5, wherein "2θ" represents diffraction angle, "d" represents the distance between crystal planes, and "I/Io" represents the relative intensity of peaks. The analysis was carried out using D/MAX-2200V X-ray Diffractometer (XRD; Rigaku).

TABLE 2

Example 1 (Metformin malonate)

| 2θ (±0.2) | d | I/Io |
|---|---|---|
| 9.5 | 9.03 | 399 |
| 12.4 | 7.12 | 211 |
| 15.6 | 5.67 | 342 |
| 16.1 | 5.51 | 476 |
| 16.4 | 5.41 | 501 |
| 17.6 | 5.04 | 217 |
| 19.1 | 4.65 | 730 |
| 20.2 | 4.38 | 310 |
| 20.7 | 4.29 | 404 |
| 22.2 | 4.00 | 358 |
| 25.1 | 3.55 | 665 |
| 25.9 | 3.43 | 370 |
| 27.9 | 3.20 | 369 |
| 28.7 | 3.10 | 1000 |

TABLE 3

Example 2 (Metformin glutarate)

| 2θ (±0.2) | d | I/Io |
|---|---|---|
| 11.8 | 7.49 | 399 |
| 12.7 | 6.95 | 200 |
| 18.1 | 4.89 | 806 |
| 18.8 | 4.72 | 459 |
| 20.7 | 4.30 | 291 |
| 22.3 | 3.98 | 390 |
| 23.2 | 3.82 | 334 |
| 23.7 | 3.75 | 526 |
| 25.2 | 3.52 | 444 |
| 27.2 | 3.28 | 267 |
| 28.1 | 3.17 | 633 |
| 29.1 | 3.07 | 257 |
| 29.5 | 3.03 | 369 |
| 32.5 | 2.75 | 256 |
| 34.3 | 2.61 | 272 |
| 35.7 | 2.51 | 310 |
| 17.6 | 5.02 | 1000 |

TABLE 4

Example 15 (Metformin adipate)

| 2θ (±0.2) | d | I/Io |
|---|---|---|
| 11.2 | 7.91 | 298 |
| 15.9 | 5.58 | 363 |
| 20.3 | 4.38 | 544 |
| 21.3 | 4.17 | 444 |
| 22.3 | 3.98 | 719 |
| 24.3 | 3.66 | 958 |
| 26.5 | 3.37 | 361 |
| 26.8 | 3.33 | 524 |
| 28.4 | 3.14 | 415 |
| 30.2 | 2.96 | 230 |
| 18.6 | 4.77 | 1000 |

TABLE 5

Example 22 (Metformin malate)

| 2θ (±0.2) | d | I/Io |
|---|---|---|
| 29.7 | 3.01 | 409 |
| 29.9 | 2.99 | 495 |
| 18.6 | 4.76 | 1000 |

Experimental Example 2

Measurement of Melting Point

The melting point (222.8-224.0° C.) of metformin hydrochloride and the melting points of metformin malonate, metformin glutarate, metformin adipate and metformin malate of formula 1 synthesized in Examples 1, 2, 15 and 23, respectively, were measured with a melting point meter (IA9100 MK1, Barnstead, UK), and the measured results are shown in Table 6 below.

TABLE 6

Comparison of melting point between metformin hydrochloride and metformin dicarboxylate

| Entry | Name | melting point (° C.) |
|---|---|---|
| 1 | Metformin hydrochloride | 222.8~224.0 |
| 2 | Metformin malonate | 191.4~192.0 |
| 3 | Metformin glutarate | 195.0~200.0 |

TABLE 6-continued

Comparison of melting point between metformin hydrochloride and metformin dicarboxylate

| Entry | Name | melting point (° C.) |
|---|---|---|
| 4 | Metformin adipate | 200.0~205.0 |
| 5 | Metformin malate | 215.0~218.0 |

Experimental Example 3

Nuclear Magnetic Resonance Analysis (1H-NMR, 1C-NMR)

Metformin malonate, metformin glutarate, metformin adipate and metformin malate synthesized in Examples 1, 2, 15 and 23, respectively, were measured for $^1$H, $^{13}$C-nuclear magnetic resonance spectra at 600 MHz (Varian-Inova 600). The measured spectra are shown in FIGS. 1, 2, 3 and 4, and the data of the respective signals are shown in Table 7 below. Herein, as the solvent in the nuclear magnetic resonance analysis, deuterium-substituted water (D$_2$O) was used.

TABLE 7

| | |
|---|---|
| Metformin hydrochloride | $^1$H-NMR (600 MHz, D$_2$O) δ (ppm) 2.941 (s, 12H, N—(CH$_3$)$_2$), 3.015 (s, 2H, —CO—CH$_2$—CO—), $^{13}$C-NMR (600 MHz, D$_2$O) δ (ppm) 37.484 (N—(CH$_3$)$_2$), 47.835 (—CO—CH$_2$—CO—), 158.570 (—C=N—), 160.076 (—C=N—), 177.303 (—C=O) |
| Metformin glutarate | $^1$H-NMR (600 MHz, D$_2$O) δ (ppm) 3.02 (s, 12H, N—(CH$_3$)$_2$), 1.48 (s, 4H, NH$_2$), 2.15 (t, 4H, CH$_2$), 1.76 (p, 2H, CH$_2$), 1.32 (s, 2H, CH) $^{13}$C-NMR (600 MHz, D$_2$O) δ (ppm) 37.496 (N—(CH$_3$)$_2$), 160.16 (—C=N—), 158.55 (—C=N—), 183.22 (—C=O), 23.14 (COCH$_2$CH$_2$—) |
| Metformin adipate | $^1$H-NMR (600 MHz, D$_2$O) δ (ppm) 3.012 (s, 12H, N—(CH$_3$)$_2$), 2.159 (s, 4H, CO—CH$_2$—C—), 1.52 (s, 4H, —C—CH$_2$—C—) $^{13}$C-NMR (600 MHz, D$_2$O) δ (ppm) 25.994 (COCH$_2$CH$_2$—), 37.496 (N—(CH$_3$)$_2$), 158.55 (—C=N—) 160.166 (—C=N—), 183.84 (—C=O) |
| Metformin malate | $^1$H-NMR (600 MHz, D$_2$O) δ (ppm) 2.274-2.231 (q, 1H, CO—CH$_2$—CH), 2.559-2.553 (d, 0.5H, CO—CH$_2$—CH), 2.584-2.579 (d, 0.5H, CO—CH$_2$—CH), 2.977 (s, 12H, N—(CH$_3$)$_2$), 4.193-4.188 (d, 0.5H, OH—CH—CO), 4.210-4.206 (d, 0.5H, OH—CH—CO) $^{13}$C-NMR (600 MHz, D$_2$O) δ (ppm) 37.50 (—COCH$_2$COH), 42.75 (N—(CH$_3$)$_2$), 70.46 (—CO—OH), 158.56 (—C=NH), 160.13 (—C=NH), 179.79 (—C=O), 181.01 (—C=O) |

Experimental Example 4

Solubility Test

Figure 5:
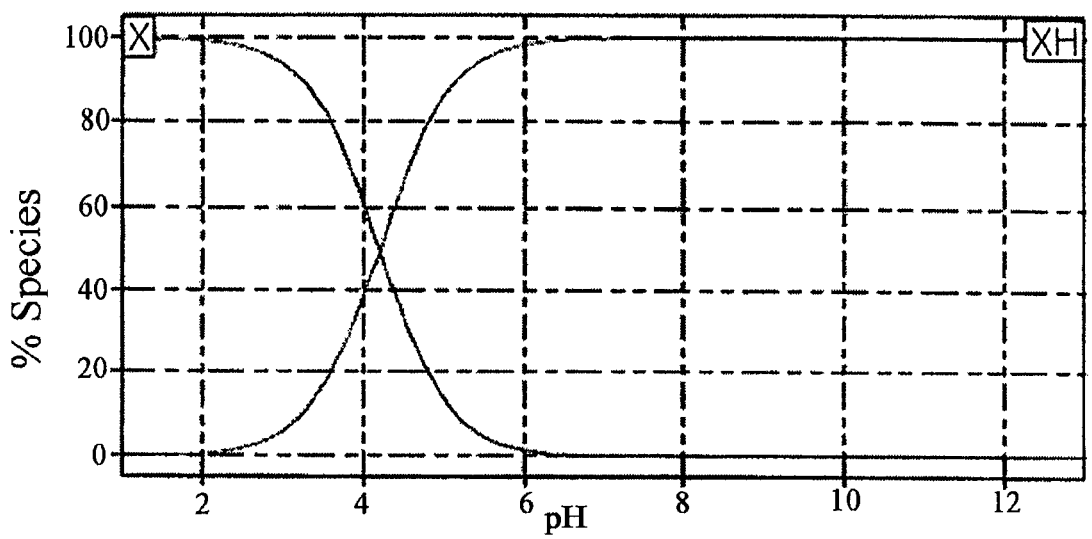
FIG. 5 shows the pKa value of metformin glutarate prepared in Example 2.
Figure 6:
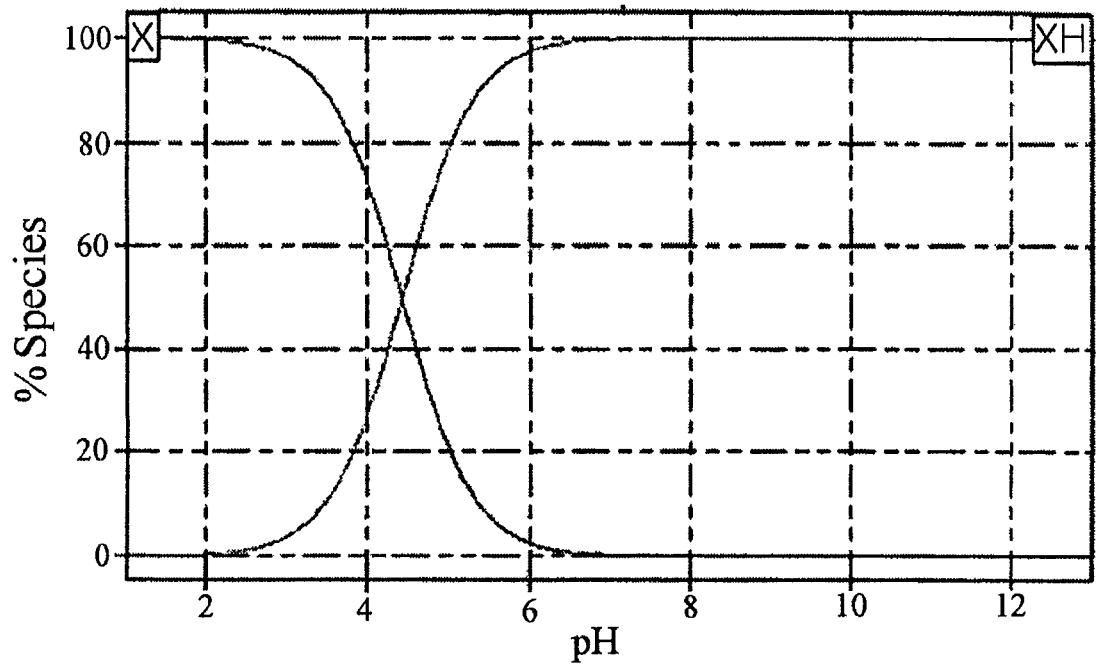
FIG. 6 shows the pKa value of metformin adipate prepared in Example 14.
Figure 7:
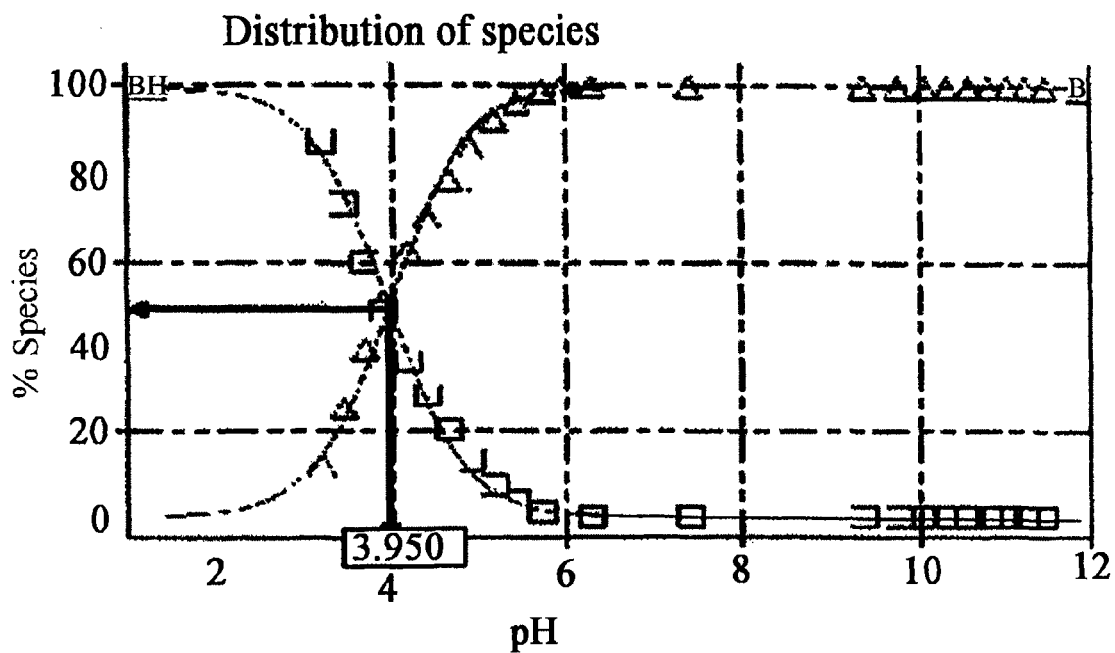
FIG. 7 shows the pKa value of metformin malate prepared in Example 22.

Metformin malonate, metformin glutarate, metformin adipate and metformin malate synthesized in Examples 1, 2, 15 and 23, respectively, were measured for saturated solubility and pH at saturation were measured. The measured results are shown in Table 8 below and FIGS. 5, 6 and 7.

The solubility test of metformin malonate was carried out according to the method disclosed in the Korean Pharmacopeia by dissolving the compound in distilled water until saturation, and then analyzing the solution by liquid chromatography to measure the amount of the dissolved compound on the basis of the metformin free-base. In addition, the solubilities of metformin glutarate, metformin adipate and metformin malate were measured in pure water using a Nephelometer in DMSO-free conditions.

TABLE 8

| Salt of Metformin | Saturated solubility (mg/mL) | Saturation pH |
|---|---|---|
| Metformin hydrochloride | 360 | 2.892 |
| Metformin malonate | 257 | 10.690 |
| Metformin glutarate | 1148 | 10.200 |
| Metformin adipate | 870 | 6.600 |
| Metformin malate | 290 | 3.950 |

Experimental Example 5

Quantitative Analysis by Mass Spectrometer

Metformin glutarate, metformin adipate and metformin malate of formula 1 synthesized in Examples 2, 15 and 23, respectively, were analyzed using a mass spectrometer (Applied Biosystems, Inc. API 3000), and the analyzed date are as follows.

The metformin malate had m/z=130.11 [MH$^+$], which is a molecular weight corresponding to the mass of metformin free-base, and fragment ions of 60.05, 71.05, 85.04, 88.08, 113.08 and 130.1 coincided with cleavage modes inferred in the same chemical structures.

Experimental Example 6

Qualitative Analysis of Metformin Malonate

Metformin malonate of formula 1, prepared in Example 1, and known metformin hydrochloride, were continuously exposed to conditions of temperature of 40° C. and relative humidity of 75% for each of 1, 2 and 5 days, and then the water content thereof was measured with Karl-Fisher moisture meter. The measured results are shown in Table 9 below. In Table 9, the measured values are expressed as the content (wt %) of water in the active ingredient. In addition, the compound was tested in conditions of temperature 60° C. and relative humidity of 15%, which had no moisture, to measure the dissociation degree of water of crystallization in the hydrate, thus examining whether the hydrate is a stable hydrate which does not release water of crystallization.

TABLE 9

| Temp., R.H. | Time (Day) | Metformin malonate | Metformin hydrochloride |
|---|---|---|---|
| 40° C., 75% | 0 | 5.143 | 0.080 |
| | 1 | 5.403 | 0.069 |
| | 2 | 5.288 | 0.053 |
| | 5 | 5.376 | 0.054 |

TABLE 9-continued

| Temp., R.H. | Time (Day) | Metformin malonate | Metformin hydrochloride |
|---|---|---|---|
| 60° C., 15% | 0 | 5.143 | 0.080 |
| | 1 | 5.222 | 0.044 |
| | 2 | 5.219 | 0.047 |
| | 5 | 5.184 | 0.056 |

As can be seen in Table 9 above, it was found that the metformin malonate hydrate of formula 1 was a non-hygroscopic salt which does not absorb water even in high-humidity conditions, in the same manner as the known metformin hydrochloride, and it was a stable hydrate which does not release water of crystallization even in low-humidity conditions.

Experimental Example 7

Test of Effect of Metformin Malonate

Metformin malonate synthesized in Example 1 of the present invention was administered orally to hyperlipidemia-induced rats for 1 week, and the lipid-reducing effect thereof was observed. The test method is shown in brief in Table 10 below.

TABLE 10

| Title | Evaluation of effect on blood lipid when metformin malonate and the like were administered orally for 1 week to rats in which hyperlipidemia has been induced by feeding cholesterol diets. |
|---|---|
| Object | To evaluate the hyperlipidemia-reducing effect of metformin dicarboxylates |
| Test system | Species: SD rats (having no specific pathogen)<br>Old: 5-week-old when purchased, and 10-week-old when administered with the compounds<br>Sex: male<br>Number of animals used: 12 animals for each group |
| Test groups | 1) group administered with metformin malonate (500 mg/kg)<br>2) group administered with metformin hydrochloride (500 mg/kg)<br>3) control group (negative control group) |
| Test method | 1) the rats were fed with hyperlipidemia-inducing feed (AIN-76, 1% cholesterol, 0.5% cholic acid) for 4 weeks.<br>2) a small amount of blood was collected from the tail vein of the rats and subjected to blood biochemical tests, and hyperlipidemia-induced rats were selected and separated.<br>3) each of metformin malonate and metformin hydrochloride was administered orally to the hyperlipidemia-induced rats at a dose of 500 mg/kg for 1 week. Also, untreated group administered with no drug was separately established.<br>4) after one week, blood was collected from the rats and subjected to blood chemical tests to evaluate the lipid reducing effects of the compounds. |
| Statistical analysis | Each of the test groups was subjected to dispersive analysis, and then to Dunnett t-test. |

The blood biochemical test results obtained in this experiment are shown in Table 11 below.

TABLE 11

| | Metformin malonate* | Metformin hydrochloride* | Control group* |
|---|---|---|---|
| AST (IU/L) | 136.6 ± 11.6 | 126.9 ± 8.4 | 158.0 ± 6.3 |
| ALT (IU/L) | 49.0 ± 7.0 | 49.8 ± 4.8 | 41.3 ± 4.2 |
| BUN(mg/dl) | 15.3 ± 0.9 | 13.6 ± 0.4 | 14.9 ± 0.7 |
| CRE (mg/dl) | 0.5 ± 0.0 | 0.5 ± 0.0 | 0.5 ± 0.0 |
| CHO(mg/dl) | 238.2 ± 16.4 | 277.1 ± 21.8 | 371.4 ± 41.3 |
| TG (mg/dl) | 50.3 ± 7.9 | 37.3 ± 1.5 | 45.2 ± 3.5 |
| LDL(mg/dl)[†] | 168.3 ± 13.7 | 198.3 ± 18.5 | 274.3 ± 30.7 |
| HDL(mg/dl) | 40.4 ± 1.4 | 42.5 ± 1.0 | 43 ± 2.1 |

AST: Aspartate Aminotransferase
ALT: Alanine Aminotransferase
BUN: Blood area nitrogen
CRE: cAMP responsive element
CHO: Cholesterol
TG: Triglyceride
LDL: Low density lipoprotein
HDL: High density lipoprotein
*Average ± Standard deviation 1. There was no statistically significant difference in AST and ALT levels between the metformin malonate-administered group and the metformin hydrochloride-administered group. Also, there was no statistically significant difference in BUN and CRE levels between the two groups.

2. When metformin malonate was administered, the blood cholesterol level in the administered group was reduced by an average of 35.86%, which was lower by 14.04% than in the group administered with metformin hydrochloride. These test results suggest that metformin malonate is superior to the existing metformin hydrochloride with respect to the cholesterol-reducing effect.

3. The triglyceride level in the group administered with metformin malonate was slightly higher than those in the control group and the metformin hydrochloride-administered group, but it was not statistically significantly different from those in the control group and the metformin hydrochloride-administered group.

4. The blood LDL level was significantly lower in the metformin malonate-administered group than the other groups. It was lower by 38.64% than the control group and by 15.13% than the metformin hydrochloride-administered group.

5. There was no significant difference in blood HDL level between the groups.

In conclusion, metformin malonate is a safe compound that does not change liver values or urine levels, and it is an excellent compound that lowers the blood cholesterol and LDL levels compared to the existing metformin hydrochloride.

Experimental Example 8

Determination of Composition

To confirm and analyze the structural composition of metformin glutarate and metformin adipate, the following test was carried out.

Using the molecular weight values shown in Tables 12 and 13 below, the free bases of metformin glutarate and metformin hydrochloride were analyzed comparatively with the area of HPLC. As a result, it was found that the free bases coincided with the area.

Figure 8:
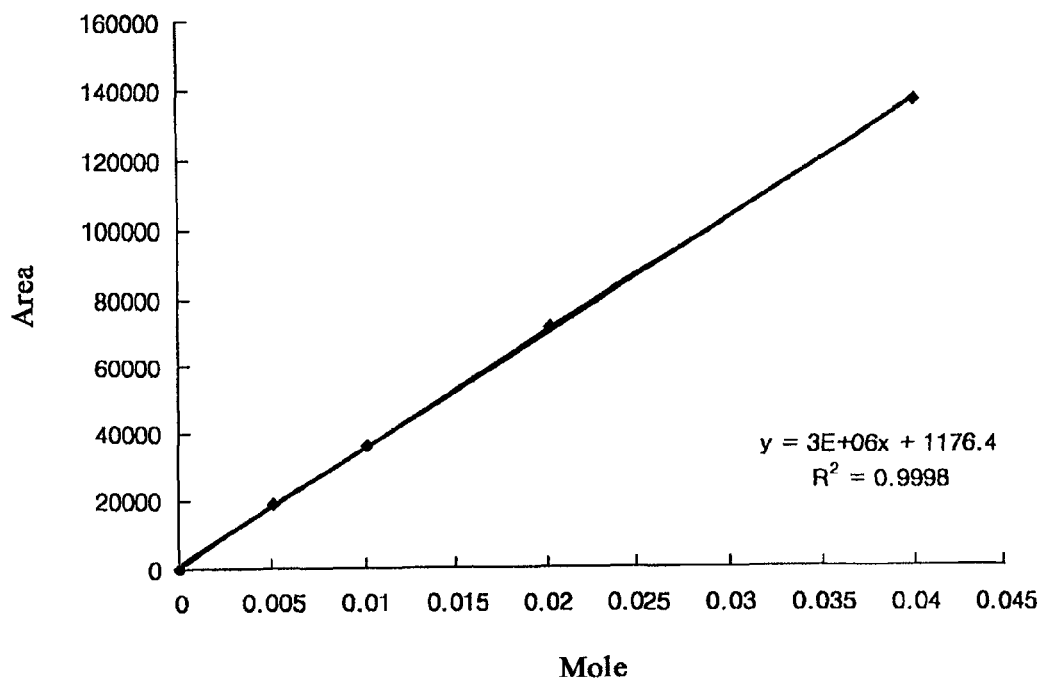
FIG. 8 shows the results of Experimental Example 8, which indicate that metformin glutarate is concentration-dependent.
Figure 9:
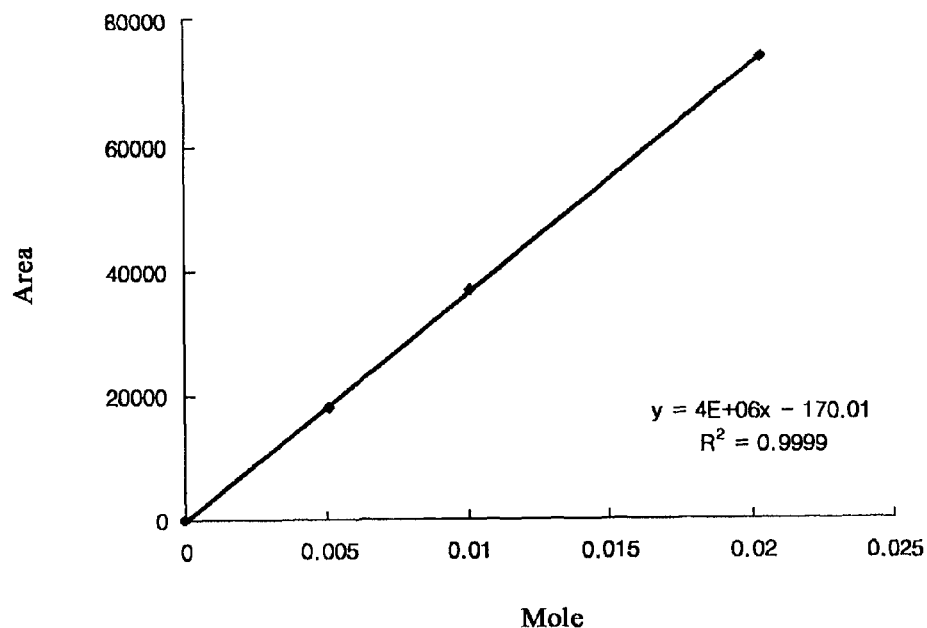
FIG. 9 shows the results of Experimental Example 8, which show that metformin adipate is concentration-dependent.

FIGS. 8 and 9 show that Example 2 (metformin glutarate) and Example 15 (metformin adipate), each having a composition of 2:1, are concentration-dependent.

TABLE 12

| Metformin glutarate | | |
|---|---|---|
| mole/area | (2:1) | Comparison (%) |
| Metformin glutarate | 7473.5 | 95.84 |
| Metformin free base | 7798 | 100 |

TABLE 13

| Metformin adipate | | |
|---|---|---|
| mole/area | (2:1) | Comparison (%) |
| Metformin adipate | 7888.5 | 98.84 |
| Metformin free base | 7798 | 100 |

Because metformin glutarate and metformin adipate, which are ionized, act as an acidic, basic or amphoteric compound depending on pH, the change in pH at each titration point occurs. Thus, pKa values calculated from the difference between calculated pH values and actually measured pH values are as follows.

TABLE 14

| Metformin glutarate | pKa | Deviation | Temperature (° C.) |
|---|---|---|---|
| First | 4.181 | 0.032 | 29.18 |
| Second | 4.181 | 0.035 | 28.83 |
| Third | 4.181 | 0.046 | 28.78 |

TABLE 15

| Metformin adipate | pKa | Deviation | Temperature (° C.) |
|---|---|---|---|
| First | 4.411 | 0.029 | 28.79 |
| Second | 4.411 | 0.029 | 28.77 |
| Third | 4.411 | 0.04 | 28.80 |

Experimental Example 10

Elemental Analysis (EA)

Metformin adipate and metformin malate, synthesized in Examples 15, 23 and 31, respectively, were subjected to elemental analysis using FISONS EA-1108 Elemental Analyzer for C, H and N and Thermo Finnigan FLASH EA-1112 Elemental Analyzer for O. The analysis results are shown in Tables 16, 17 and 18.

TABLE 16

| Analysis subject | C (%) | H (%) | N (%) | O (%) |
|---|---|---|---|---|
| Metformin adipate divalent theoretical value (anhydride) | 41.57 | 7.97 | 34.63 | 15.82 |
| Metformin adipate measured value | 41.8 | 8.0 | 35.0 | 15.4 |

The results of the elemental analysis revealed that metformin adipate of the present invention coincided with the theoretical values for an anhydride having a molecular formula of $C_{14}H_{32}N_{10}O_4$.

TABLE 17

| Analysis subject | O (%) | H (%) | H (%) | O (%) |
|---|---|---|---|---|
| Metformin malate divalent theoretical value (¼ anhydride) | 36.31 | 7.24 | 35.29 | 21.16 |
| Metformin malate measured value | 36.5 | 7.1 | 35.5 | 21.5 |

The results of the elemental analysis revealed that metformin malate of the present invention coincided with the theoretical values for one $H_2O$ molecule per four molecules having a molecular formula of $C_{12}H_{28}N_{10}O_5$.

TABLE 18

| Analysis subject | C (%) | H (%) | N (%) | O (%) |
|---|---|---|---|---|
| Metformin malate divalent theoretical value | 36.73 | 7.19 | 35.69 | 20.39 |
| Metformin malate measured value | 36.3 | 7.2 | 35.2 | 19.9 |

The results of the elemental analysis revealed that metformin malate of the present invention coincided with theoretical values for an anhydride having a molecular formula of $C_{12}H_{28}N_{10}O_5$.

Experimental Example 11

IR Spectrum

Figure 10:
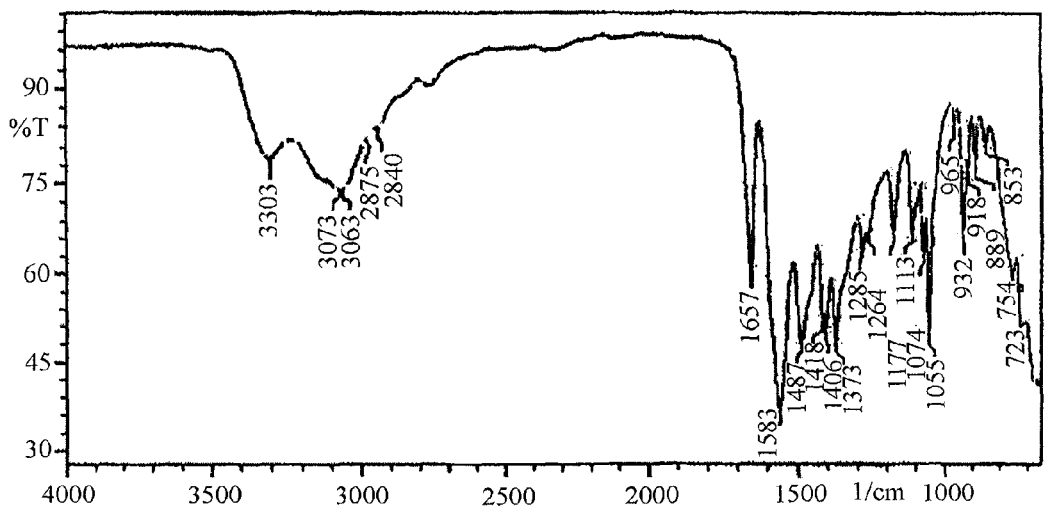
FIG. 10 shows the positions of major absorption bands and absorption peaks, measured for metformin malate using IR-spectrum (TRAVEL-IR, SENSIR, TECHNOLOGIES/US).

The IR spectrum of metformin malate synthesized in Example 23 was measured with TRAVEL-IR (SENSIR, TECHNOLOGIES/US), and the positions of the obtained main absorption bands and the results of the obtained absorption peaks are shown in Table 19 and FIG. 10.

TABLE 19

| Frequency (cm$^{-1}$) | Imputation |
|---|---|
| 3303 | N—H Stretching oscillation |
| 1657 | C=N Stretching oscillation |
| 1563 | NH$_2$ Torsional oscillation |
| 1373 | CH$_3$ Torsional oscillation |
| 1285 | C—O Stretching oscillation |

Experimental Example 12

Differential Scanning Calorimetry Analysis

Figure 11:
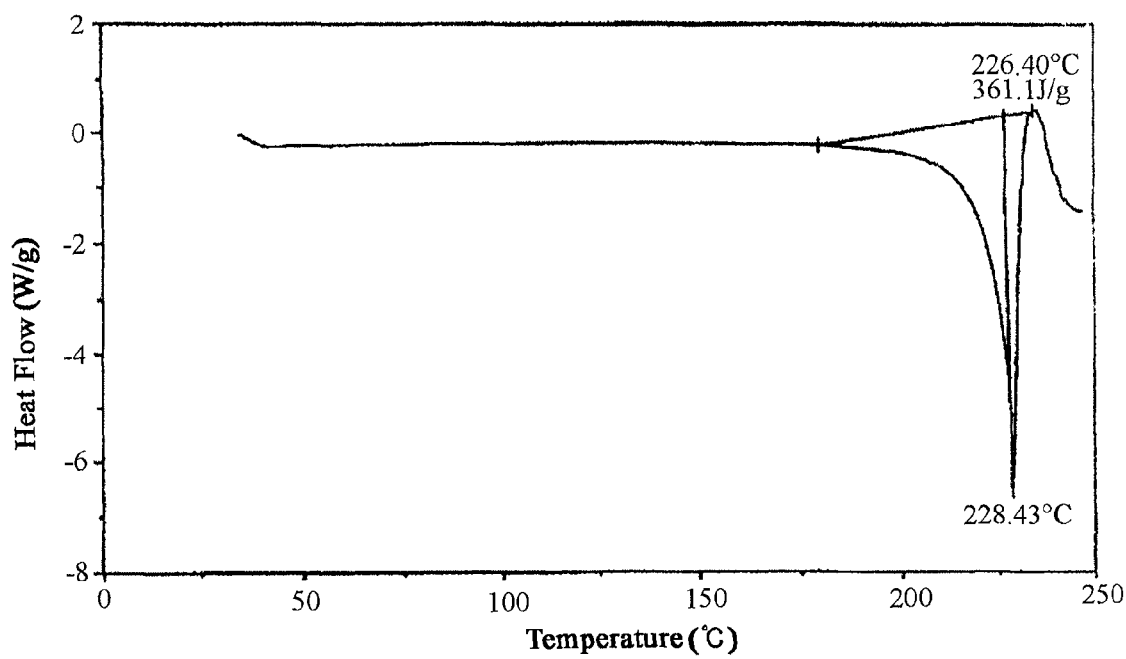
FIG. 11 shows the results of differential scanning calorimetry analysis (TA instruments DSC 2910 MDSC V4.4E/US) of metformin malate.

Metformin malate synthesized in Example 23 was subjected to differential scanning calorimetry analysis (TA instruments DSC 2910 MDSC V4.4E/US), and the analysis results are shown in FIG. 11. As can be seen in FIG. 11, the drug showed endothermic peaks resulting from decomposition at around 226.4° C.

The invention claimed is:

1. A metformin (2:1) malonate represented by the following Formula 1:

[Formula 1]

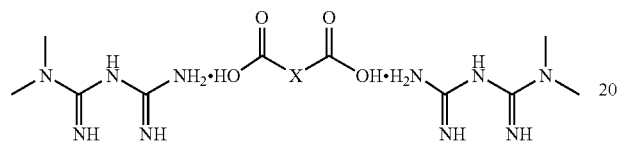

wherein X is —(CH$_2$)—;

wherein the metformin (2:1) malonate is in a crystalline form having X-ray diffraction peaks at 9.5±0.2, 16.1±0.2, 16.4±0.2, 19.1±0.2, 20.7±0.2, 25.1±0.2, and 28.7±0.2 degrees 2θ; and, wherein most intense peak in the X-ray diffraction pattern is the peak at 28.7±0.2.

2. The metformin (2:1) malonate of claim 1, which is in the form of a hydrate.

3. The metformin (2:1) malonate of claim 1, wherein the metformin (2:1) malonate has a melting point of from about 191.4 to about 192.0° C.

4. A pharmaceutical composition comprising an effective amount of the metformin (2:1) malonate of claim 1.

* * * * *